(12) United States Patent
Potharaju et al.

(10) Patent No.: US 11,497,877 B2
(45) Date of Patent: *Nov. 15, 2022

(54) INTEGRATED HUMIDIFIER CHAMBER AND LID

(71) Applicant: Fisher & Paykel Healthcare Limited, Auckland (NZ)

(72) Inventors: Venkata Subbarao Potharaju, Auckland (NZ); Christie Jayne Stanton, Auckland (NZ); Andrew Paul Maxwell Salmon, Auckland (NZ); Yi-Cheng Sun, Auckland (NZ); Hayden Briscoe, Auckland (NZ); Samuel Frew, Auckland (NZ); Steven John Worthington, Auckland (NZ); Philip John Dickinson, Auckland (NZ); Cameron Jon Haxton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 452 days.

This patent is subject to a terminal disclaimer.

(21) Appl. No.: 16/185,538

(22) Filed: Nov. 9, 2018

(65) Prior Publication Data

US 2019/0143069 A1    May 16, 2019

Related U.S. Application Data

(63) Continuation of application No. 14/053,352, filed on Oct. 14, 2013, now Pat. No. 10,155,097, which is a
(Continued)

(30) Foreign Application Priority Data

Jul. 30, 2007  (NZ) ........................ 560235

(51) Int. Cl.
*A61M 16/08*    (2006.01)
*A61M 16/10*    (2006.01)
(Continued)

(52) U.S. Cl.
CPC ........ *A61M 16/0816* (2013.01); *A61M 16/10* (2013.01); *A61M 16/109* (2014.02);
(Continued)

(58) Field of Classification Search
CPC .............. A61M 16/00; A61M 16/0057; A61M 16/0066; A61M 16/04; A61M 16/08;
(Continued)

(56) References Cited

U.S. PATENT DOCUMENTS 3,587,896 A   6/1971  Graff
3,659,604 A   5/1972  Melville et al.
(Continued)

FOREIGN PATENT DOCUMENTS

CA    2151992       6/1996
CN    1491123 A    4/2004
(Continued)

OTHER PUBLICATIONS

Canadian Examination Report; dated Jan. 16, 2019; 3 pages.
(Continued)

*Primary Examiner* — Colin W Stuart
(74) *Attorney, Agent, or Firm* — Knobbe, Martens, Olson & Bear, LLP

(57) ABSTRACT

A blower unit for use as part of an integrated blower/humidification system is described. The blower unit has an outer casing, which encloses and forms part of the blower unit, the casing including an air inlet vent. The blower unit further includes a humidifier compartment for receiving a humidifier unit with a separate gases inlet and outlet, the compartment having a heater base for heating the contents of
(Continued)

the humidifier unit. The compartment also has a blower inlet port which aligns with the humidifier unit inlet in use, the blower providing a gases path through the casing between the inlet vent and the inlet port. The blower unit also includes a fan for providing a pressurised gases stream along the gases path, and a power supply unit for powering the fan. The gases path is routed over the power supply unit in order to provide a cooling air flow.

20 Claims, 19 Drawing Sheets

Related U.S. Application Data continuation of application No. 12/513,752, filed as application No. PCT/NZ2007/000328 on Oct. 31, 2007, now Pat. No. 8,555,879.

(60) Provisional application No. 60/864,501, filed on Nov. 6, 2006.

(51) Int. Cl.
  *A61M 39/10* (2006.01)
  *A61M 16/16* (2006.01)
  *A61M 16/00* (2006.01)

(52) U.S. Cl.
  CPC ........ *A61M 16/1075* (2013.01); *A61M 16/16* (2013.01); *A61M 39/1055* (2013.01); *A61M 16/0066* (2013.01); *A61M 2039/1022* (2013.01); *A61M 2039/1033* (2013.01); *A61M 2205/36* (2013.01); *A61M 2205/362* (2013.01); *A61M 2205/3653* (2013.01); *A61M 2205/502* (2013.01)

(58) Field of Classification Search
  CPC .......... A61M 16/0816; A61M 16/0825; A61M 16/0833; A61M 16/0875; A61M 16/0883; A61M 16/1075; A61M 16/16; A61M 39/10; A61M 39/105; A61M 39/1055; A61M 2039/1033; A61M 2039/1022; F16L 27/00–27/12751
  USPC .................................................. 285/272–282
  See application file for complete search history.

(56) References Cited

U.S. PATENT DOCUMENTS

| | | | |
|---|---|---|---|
| 3,806,102 A | 4/1974 | Valenta et al. | |
| 3,917,757 A | 11/1975 | Hoag | |
| 4,028,444 A | 6/1977 | Brown et al. | |
| 4,060,576 A | 11/1977 | Grant | |
| 4,098,853 A | 7/1978 | Brown et al. | |
| 4,152,379 A | 5/1979 | Suhr | |
| 4,164,219 A * | 8/1979 | Bird ...................... | A61M 16/00 128/204.19 |
| 4,203,027 A | 5/1980 | O-Hare et al. | |
| 4,333,451 A * | 6/1982 | Paluch ............... | A61M 16/0808 128/205.12 |
| 4,588,425 A | 5/1986 | Usry et al. | |
| 4,753,758 A | 6/1988 | Miller | |
| 4,955,372 A | 9/1990 | Blackmer | |
| 5,117,819 A | 6/1992 | Servidio et al. | |
| 5,231,979 A | 8/1993 | Rose et al. | |
| 5,558,084 A | 9/1996 | Daniell et al. | |
| 5,588,423 A | 12/1996 | Smith | |
| 5,598,838 A | 2/1997 | Servidio et al. | |
| 5,640,951 A * | 6/1997 | Huddart ................ | A61M 16/08 128/204.17 |
| 5,673,687 A | 10/1997 | Dobson et al. | |
| 5,971,369 A | 10/1999 | Neveu et al. | |
| 6,085,752 A | 7/2000 | Kehr et al. | |
| 6,126,721 A | 10/2000 | Nemser et al. | |
| 6,149,141 A | 11/2000 | Birdsell et al. | |
| D453,567 S | 2/2002 | Voegele et al. | |
| 6,349,724 B1 | 2/2002 | Burton et al. | |
| 6,435,180 B1 | 8/2002 | Hewson et al. | |
| 6,460,538 B1 | 10/2002 | Kemp | |
| 6,812,435 B2 | 11/2004 | Schilling | |
| D504,945 S | 5/2005 | Van Brunt | |
| 6,935,337 B2 | 8/2005 | Virr et al. | |
| 6,953,354 B2 | 10/2005 | Edirisuriya et al. | |
| 7,096,864 B1 | 8/2006 | Mayer et al. | |
| 7,111,624 B2 | 9/2006 | Thudor et al. | |
| 7,137,388 B2 | 11/2006 | Virr et al. | |
| 7,314,046 B2 | 1/2008 | Schroeder et al. | |
| D561,890 S | 2/2008 | Liethgow et al. | |
| 7,409,952 B2 | 8/2008 | Chen | |
| 7,413,173 B2 | 8/2008 | DiMatteo et al. | |
| 7,439,835 B2 | 10/2008 | Dietrich et al. | |
| 7,463,556 B2 | 12/2008 | Hocherman | |
| 7,478,634 B2 | 1/2009 | Jam | |
| 7,478,635 B2 | 1/2009 | Wixey et al. | |
| 7,617,823 B2 | 11/2009 | DiMatteo et al. | |
| 7,677,246 B2 | 3/2010 | Kepler | |
| 7,754,157 B2 | 7/2010 | Tomioka | |
| 7,789,194 B2 | 9/2010 | Lathrop et al. | |
| 7,909,032 B2 | 3/2011 | Feldhahn et al. | |
| 7,958,892 B2 | 6/2011 | Kwok et al. | |
| 8,006,691 B2 | 8/2011 | Kenyon et al. | |
| D646,665 S | 10/2011 | Iijima | |
| 8,225,796 B2 | 7/2012 | Davenport et al. | |
| 8,555,879 B2 | 10/2013 | Potharaju | |
| 8,905,023 B2 | 12/2014 | Niland et al. | |
| 9,220,865 B2 | 12/2015 | Potharaju et al. | |
| 9,579,480 B2 | 2/2017 | Potharaju et al. | |
| D798,437 S | 9/2017 | Buckley et al. | |
| 10,155,097 B2 | 12/2018 | Potharaju et al. | |
| 10,195,389 B2 | 2/2019 | Virr et al. | |
| 10,201,676 B2 | 2/2019 | Lithgow et al. | |
| 10,850,053 B2 | 12/2020 | Kenyon et al. | |
| 10,881,820 B2 | 1/2021 | Crumblin et al. | |
| 10,898,670 B2 * | 1/2021 | Potharaju ............ | A61M 16/109 |
| 11,040,166 B2 | 6/2021 | Virr et al. | |
| 11,235,115 B2 | 2/2022 | Crumblin et al. | |
| 11,298,499 B2 | 4/2022 | Bath et al. | |
| 2003/0066526 A1 | 4/2003 | Thudor et al. | |
| 2003/0236015 A1 | 12/2003 | Edirisuriya | |
| 2004/0016430 A1 | 1/2004 | Makinson et al. | |
| 2004/0034287 A1 | 2/2004 | Hickle | |
| 2004/0045909 A1 | 3/2004 | Tomioka et al. | |
| 2004/0055597 A1 | 3/2004 | Virr et al. | |
| 2004/0133915 A1 | 7/2004 | Jean-Pierre | |
| 2004/0206352 A1 | 10/2004 | Conroy, Jr. | |
| 2004/0226562 A1 | 11/2004 | Bordewick | |
| 2005/0103339 A1 | 5/2005 | Daly et al. | |
| 2005/0165543 A1 | 7/2005 | Yokota | |
| 2005/0205395 A1 | 9/2005 | Dietrich et al. | |
| 2005/0268910 A1 | 12/2005 | Nord et al. | |
| 2006/0055069 A1 | 3/2006 | DiMatteo et al. | |
| 2006/0111749 A1 | 5/2006 | Westenskow et al. | |
| 2006/0191531 A1 | 8/2006 | Mayer et al. | |
| 2007/0023044 A1 | 2/2007 | Kwok et al. | |
| 2007/0048159 A1 | 3/2007 | DiMatteo et al. | |
| 2007/0070033 A1 | 3/2007 | Guerraz et al. | |
| 2007/0163600 A1 * | 7/2007 | Hoffman ............ | A61M 16/0683 128/207.18 |
| 2007/0169776 A1 | 7/2007 | Kepler et al. | |
| 2007/0193580 A1 | 8/2007 | Feldhahn et al. | |
| 2007/0193582 A1 | 8/2007 | Kwok et al. | |
| 2007/0272245 A1 | 11/2007 | Ripple et al. | |
| 2008/0072900 A1 | 3/2008 | Kenyon | |
| 2008/0099017 A1 | 5/2008 | Bordewick et al. | |
| 2008/0142019 A1 | 6/2008 | Lewis et al. | |
| 2008/0190427 A1 | 8/2008 | Payton et al. | |
| 2008/0200868 A1 | 8/2008 | Alberti et al. | |
| 2008/0245365 A1 | 10/2008 | Genger et al. | |
| 2008/0257346 A1 | 10/2008 | Lathrop et al. | |
| 2008/0300572 A1 | 12/2008 | Rankers et al. | |

(56) References Cited

U.S. PATENT DOCUMENTS

| | | |
|---|---|---|
| 2009/0194106 A1 | 8/2009 | Smith et al. |
| 2009/0229606 A1 | 9/2009 | Tang et al. |
| 2010/0024816 A1 | 2/2010 | Weinstein et al. |
| 2010/0236552 A1* | 9/2010 | Kwok ............... A61M 16/0003 128/204.21 |
| 2011/0154241 A1 | 6/2011 | Skidmore et al. |
| 2011/0186048 A1 | 8/2011 | Casse |
| 2012/0240927 A1 | 9/2012 | Bathe et al. |
| 2014/0137866 A1 | 5/2014 | Potharaju et al. |
| 2017/0209664 A1 | 7/2017 | Potharaju et al. |
| 2021/0196919 A1 | 7/2021 | Potharaju et al. |
| 2021/0268222 A1 | 9/2021 | Virr et al. |
| 2022/0031994 A1 | 2/2022 | Potharaju et al. |
| 2022/0126054 A1 | 4/2022 | Potharaju et al. |

FOREIGN PATENT DOCUMENTS

| | | |
|---|---|---|
| CN | 1809397 A | 7/2006 |
| DE | 9409231 U1 | 11/1994 |
| DE | 29909611 U1 | 9/1999 |
| DE | 10016005 A1 | 12/2001 |
| DE | 102005000819 B4 | 4/2016 |
| EP | 0201984 A1 | 11/1986 |
| EP | 1369141 | 12/2003 |
| EP | 1933910 B1 | 11/2016 |
| EP | 3695870 A1 | 8/2020 |
| EP | 3632493 B1 | 1/2021 |
| GB | 1301582 A | 12/1972 |
| JP | S64-500088 | 1/1989 |
| JP | 11-56725 | 10/1989 |
| JP | H05-270522 A | 10/1993 |
| JP | 09-004886 | 1/1997 |
| JP | H10-73292 A | 3/1998 |
| JP | H10-122611 A | 5/1998 |
| JP | H10-179746 | 7/1998 |
| JP | 2005-287596 | 10/2005 |
| JP | 2005-538802 | 12/2005 |
| JP | 2006-116258 A | 5/2006 |
| JP | 2006-149822 | 6/2006 |
| NZ | 590924 A | 8/2013 |
| NZ | 630757 A | 3/2016 |
| WO | WO 00/12197 | 3/2000 |
| WO | WO 2004/043528 | 3/2000 |
| WO | WO 2001/010489 | 2/2001 |
| WO | WO 2002/002169 | 1/2002 |
| WO | WO 2002/066107 | 8/2002 |
| WO | WO 2003/099363 | 12/2003 |
| WO | WO 2004/112873 | 12/2004 |
| WO | WO-2005028012 A1 * | 3/2005 ............ A61M 16/08 |
| WO | WO 2006/012877 A1 | 2/2006 |
| WO | WO 2006/031586 A1 | 3/2006 |
| WO | WO 2006/045602 A1 | 5/2006 |
| WO | WO 2006/102707 | 10/2006 |
| WO | WO 2006/107818 | 10/2006 |
| WO | WO 2006/126900 A1 | 11/2006 |
| WO | WO 2007/004898 A1 | 1/2007 |
| WO | WO 2007/019625 | 2/2007 |
| WO | WO 2007/038152 | 4/2007 |
| WO | WO 2007/045017 | 4/2007 |
| WO | WO 2008/024001 | 2/2008 |
| WO | WO 2008/056993 A2 | 5/2008 |
| WO | WO 2008/148154 A1 | 12/2008 |

OTHER PUBLICATIONS

Australian Examination Report; dated Oct. 11, 2012; 6 pages.
Australian Examination Report; dated Jan. 3, 2013; 3 pages.
Japanese Examination Report: dated May 7, 2012; 3 pages.
PCT Written Opinion of the International Searching Authority completed May 13, 2008; Nine (9) pages.
International Search Report completed on May 13, 2008; Eight (8) pages.
Chinese Examination Report and English Translation of CN Examination Report; dated Jun. 20, 2014; 12 pages.
Leventhal et al. Impact of communications on the self-regulation of health beliefs.
Examination Report for Australian Application No. 2015264874 dated Jun. 21, 2017 (4 pages).
Partial Supplementary Search Report from corresponding European Patent Application No. 07860972.4, dated Sep. 20, 2017, in 15 pages.
Australian Examination Report; dated Apr. 5, 2018; 3 pages.
Extended European Search Report from European Patent Application No. 07860972.4, dated Jan. 4, 2018, in 13 pages.
European Examination Report; dated Nov. 8, 2018; 7 pages.
Australian Examination Report; dated Nov. 15, 2018; 8 pages.
Examination report for EP Application No. 07860972.4 dated Mar. 31, 2020; 5 pages.
ResMed, Magellan IPAP® Instruction Manual, 2006; 40 pages.
ResMed Corp, Sullivan HumidAire (humidifier for use with CPAP) and user manual, 2001, 136 pages.

* cited by examiner

INTEGRATED HUMIDIFIER CHAMBER AND LID

CROSS-REFERENCE TO RELATED APPLICATIONS

This application is a continuation of U.S. patent application Ser. No. 14/053,352, filed on Oct. 14, 2013, which is continuation of U.S. patent application Ser. No. 12/513,752, filed on Oct. 14, 2009, which is a national stage application under 35 U.S.C. § 371 of International Patent Application No. PCT/NZ2007/00328, filed on Oct. 31, 2007, which claims the benefit of U.S. Provisional Application No. 60/864,501, filed Nov. 6, 2006, each of which is incorporated herein by reference in its entirety.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to a gases supply and gases humidification apparatus, particularly but not solely for providing respiratory assistance to patients or users who require a supply of humidified gas at positive pressure for the treatment of diseases such as Obstructive Sleep Apnea (OSA), snoring, or Chronic Obstructive Pulmonary Disease (COPD) and the like. In particular, this invention relates to a gases supply apparatus which has an integral humidifier chamber, so as to form a combined assisted breathing unit and humidifier.

Description of the Related Art

Devices or systems for providing a humidified gases flow to a patient for therapeutic purposes are well known in the art. Systems for providing therapy of this type, for example CPAP therapy, have a structure where gases at the required pressure are delivered from an assisted breathing unit or blower unit to a humidifier chamber downstream from the blower. As the gases are passed through the heated, humidified air in the humidifier chamber, they become saturated with water vapour. The gases are then delivered to a user or patient downstream from the humidifier, via a gases conduit. Humidified gases can be delivered from a modular system that has been assembled from separate units (that is, a system where the humidifier chamber/heater and the breathing unit/blower are separate items) connected in series via conduits. An example of a system of this type is shown in FIG. 1. However, it is becoming more common for integrated blower/humidifier systems to be used, as shown schematically in FIG. 2. A typical integrated system consists of a main 'blower' or assisted breathing unit which provides a pressurised gases flow, and a humidifier unit that mates with or is otherwise rigidly connected to the blower unit. This mating occurs for example by a slide on or push connection, so that the humidifier is held firmly in place on the main blower unit. An example of a system of this type is the Fisher and Paykel Healthcare 'slide-on' water chamber system shown and described in U.S. Pat. No. 7,111,624. A variation of this design is a slide-on or clip-on design where the chamber is enclosed inside a portion of the integrated unit in use. An example of this type of design is shown in WO 2004/112873. This specification describes a blower, or flow generator 50, and an associated humidifier 150. The blower unit 50 and the humidifier unit 150 are brought together in use and connected as described in paragraph 00119 of this document. The humidifier chamber, or water tub (698, 699, 700) is described in paragraphs 00132 to 00141. It should be noted that the water tub can either be filled through the passage 722 (described in detail in paragraph 00126), which is located on the rear wall of the humidifier unit 150, or by removing the tub lid 700. The process for removing the lid is described in paragraph 00136. When the lid of the humidifier unit (lid 648) is closed, this pushes the water tub into position.

WO 04/112873 also describes a power supply cavity, shown as item 65 in FIG. 6, and described in paragraphs [0096] and [0097]. The compartment is described as being vented to atmosphere (if necessary) for cooling. FIG. 7 shows the power supply board 124 and the cavity 65. As described in paragraph [00100], air enters the blower through an air inlet 84, communicating with passage 85 above the power supply cavity 65, with the passage then leading to the muffler cavity 134 in which the fan unit 90 sits. It should be noted that as shown in FIG. 6, the power supply cavity 65 is insulated from the air supply passage 85 and the muffler cavity 134 by two walls, with an airgap between them. Using this air flow to cool the power supply board is not discussed in this specification.

A further example of this type of design is shown in U.S. Pat. No. 7,096,864. The humidifier chamber 17 is partly enclosed in a humidifier unit 16, which is push-fitted to a separate blower or CPAP unit 1.

In the devices shown in WO 2004/112873 and U.S. Pat. No. 7,096,864, the blower unit and the humidifier unit are both discrete, 'table-standing' units, pushed together to mate pneumatically and electrically.

A further variation of the integrated blower and humidifier type of design is shown in U.S. Pat. No. 6,435,180. A water container or humidifier chamber 66 has a lid 72. The lid 72 of the humidifier chamber 66 is located in use underneath a cover 94 that covers the entire top part of the unit. Cover 94 and lid 72 can be removed simultaneously by a user passing their fingers and thumbs through the holes 92. Two separate air streams (a humidified stream and a dry stream) are mixed in the housing of the device to create one air stream that is provided to a user (Column 6, lines 23-34). It is not intended that any of the elements such as the lids or the chamber are connected together with fasteners or similar, so that the unit can be disassembled easily (column 6, lines 46-55).

A humidifier chamber with a lid is described in U.S. Pat. No. 5,588,423. Lid 11 closes the top of the chamber 2.

The advantage of these types of integrated devices is that generally they are more compact and discrete than a modular breathing circuit that has been assembled from separate units. A compact and discrete unit is particularly advantageous for home use units, where bedside space is limited, and where a user may also have to transport and set up their own personal unit elsewhere, for example if staying overnight away from home. With compact and integrated units, the set up is generally easier for a user. Generally, home units ate used for the relief of sleep apnoea. A mid-use point will usually be during the night, during a users sleep cycle. If refilling or similar is required during use, a user will need to wake up to perform this operation. Having been woken up, the user is required to remove the humidifier chamber from the integrated unit, refill it, then return it into position and if necessary reassemble the unit. Humidifier chambers are often sealed units, and cannot be easily opened. That is, they are sealed except for the inlet and outlet ports. Chambers of this type are filled through either the inlet or the outlet port of the chamber. This refilling operation can he time-consuming, difficult to perform at bedside, and can require a level of concentration that a user may find difficult to muster in the middle of the night. It is especially important to minimise disruption to a users sleep pattern if they suffer from sleep apnoea, as the intent of the therapy is to minimise disruption to their sleep patterns, and any additional factors that might disturb them are therefore unwelcome. Although chambers with lids are known in the art as described above, these are generally not designed with the intended purpose that the lid that it can be easily removed during use, for example for refilling the chamber. Humidifier chambers with removable lids are generally not designed in such a manner that simplifies this operation. It is generally intended that the lid will only be removed when the unit is not in use, to access the inner surfaces of the chamber for e.g. cleaning or similar.

Further problems can arise when filling or cleaning these units, as nearly all of the respiratory humidification systems currently available use water as a humidification medium, and cleaning will almost always be carried out with a water based cleaner. Blower and humidifier units are operated and controlled electrically, and problems can occur if the electronic parts, such as external user controls, are not protected. If the controls are not protected, any accidental water spillage that takes place can potentially short-circuit the controls and disrupt the operation of the system.

Control knobs that are designed in such a manner that the opportunities for spillage to cause damage are known in the art.

U.S. Pat. No. 6,812,435 describes a control knob for an oven that is mounted on a continuous horizontal plate, and which can be moved around on the plate. Magnetic actuators under the plate and in the knob interact, with Hall sensors detecting the changes in the magnetic fields. A control unit receives the signals from the Hall sensors and alters the output parameters of the stove accordingly. US 2005/0205395 describes a control knob arrangement where magnetic elements are embedded in the body of a knob 2, with their magnetic fields interacting as the knob is rotated with e.g. rotary field sensor 25 (a Hall sensor in the embodiment described). The knob sits in a recess 16 in a panel 14, and is held in place on the panel by retaining pegs 11 that pass through an open aperture at the bottom of the recess 16.

As outlined above, it can be difficult to concentrate and carry out complex operations in the middle of the night (or during the middle of a users sleep sequence), or if a users sleep pattern has been disrupted. It is therefore considered important, or at least preferred, that the blower and humidifier controls are as simple and intuitive as possible. Also, that the number of steps necessary to make adjustments or carry out an operation is minimised.

One of the advantages of an integrated unit is that generally they are compact and discrete, and are particularly suited for home use as their 'footprint'—e.g. on a bedside stand or similar—tends to be less than modular units. It is therefore particularly advantageous if the power supply unit can be built into, or located inside, the housing or external shell of the integrated blower/humidifier, in order to keep the 'footprint' of the unit as small as possible. However, if the power supply pack is external—located outside the housing or shell of the ventilator/humidifier unit, the heat can dissipate to atmosphere easily. If the power supply unit is located inside the shell or housing, heat from the power supply unit cannot dissipate as easily. The ventilator or 'blower' units that form part of these integrated, compact units draw a considerable amount of power. The power packs or power plants used to provide power to the motor or drive units usually generate a considerable amount of heat as a by-product of this power generation. That is, the power packs and associated circuitry (for example, transformers or similar components) become hot as a consequence of powering the operation of the ventilator/humidifier. As the temperature of the power supply increases, it works less effectively, and more power is drawn to compensate for the drop in efficiency, leading to a greater heat output, and a corresponding further drop in efficiency—a negative feedback loop. It can be seen that it is important to prevent the power supply unit from overheating, or at least from heating up to a temperature that is over the upper limit of an optimum operating range. This can be difficult to achieve if the power supply is enclosed in the external shell of an compact unit that is specifically designed to be as small as possible, with internal free space minimised. This can be especially important if the size of the power supply itself has been minimised, and the airgaps between components have been minimised, potentially leading to further difficulties with heat dissipation.

US 2007/0048159 discloses a blower unit that includes electronic circuitry (referred to generally as electronics seating portion 120). An air inlet 140 is shown directly below this electronic circuitry. It is not clear from the specification whether the electronic circuitry is heat-producing circuitry—for example, power circuitry, which generally produces a considerable amount of heat, or if it is control circuitry, which generates much less heat and does not generally require cooling. It is also unclear from the specification how the structure between the air path and the electronic circuitry is configured. The wall between the components and the air flow could potentially be thick enough to insulate the electronic circuitry from any cooling effect produced by the air flow.

Users of domestic breathing assistance apparatus (such as a CPAP device) may occasionally wish to travel and spend the night (or longer) away from home. It is normal for the breathing assistance apparatus to be carried in some form of bag or carry case. Many users prefer to have the option of carrying their device as hand luggage e.g. if flying, so that they are assured of arriving at their destination with the device. This necessitates a compact carry case (as well as a compact device). Rigid or hard carry cases are known, which allow the user a convenient safe method to travel with their device. One of the problems with any type of carry case is that when the device is placed inside is the user forgetting to empty the water from the humidification chamber. Spillages of water from the chamber can occur if the unit is packed and carried without the contents of the chamber being emptied.

It is an object of the present invention to provide a breathing assistance apparatus which goes some way to overcoming the abovementioned disadvantages or which at least provides the public or industry with a useful choice.

SUMMARY OF THE INVENTION

Accordingly in a first aspect, the invention may broadly be said to consist in a blower unit for use as part of an integrated blower/humidification system for providing heated humidified gases to a user, comprising:

an outer casing, which encloses and forms part of said blower unit, said casing including an inlet vent through which air from atmosphere can enter said casing in use, a humidifier compartment adapted to in use receive a humidifier unit of the type which has a gases inlet and a gases outlet, said compartment including a heater base adapted for use with said humidifier unit, said compartment further including a blower inlet port adapted to provide a gases path between the interior of said casing and said humidifier unit inlet in use, a gases path through said casing between said inlet vent and said blower inlet port, a fan unit contained within said casing and adapted to provide a pressurised gases stream along said gases path in use, a power supply unit located within said casing and adapted to in use provide power to said fan unit and said heater base, said gases path routed over said power supply unit in order to provide a cooling air flow.

In a second aspect, the invention may broadly be said to consist in a blower unit for use as part of an integrated blower/humidification system for providing heated humidified gases to a user, comprising:

an outer casing, which encloses and forms part of said blower unit, said casing including an inlet vent through which air from atmosphere can enter said casing in use, a humidifier compartment adapted to in use receive a humidifier unit of the type which has a gases inlet and a gases outlet, said compartment including a heater base adapted for use with said humidifier unit, said compartment further including a blower inlet port adapted to provide a gases path between the interior of said casing and said humidifier unit inlet in use, a gases path through said casing between said inlet vent and said blower inlet port, a fan unit contained within said casing and adapted to provide a pressurized gases stream along said gases path in use, a power supply unit located within said casing and adapted to in use provide power to said fan unit and said heater base, said power supply unit enclosed within a power supply sub-housing and said gases path routed so that it passes over at least two walls of said power supply sub-housing in use in order to provide a cooling air flow.

In a third aspect, the invention may broadly be said to consist in an integrated blower/humidification system for providing heated humidified gases to a user, comprising:

a humidifier unit adapted to contain a volume of water and also adapted for use in conjunction with a heater base such that said volume of water can be heated, said humidifier unit having a gases inlet port, a gases outlet port and a top fill aperture, an assisted breathing unit having an outer casing and including a humidifier compartment into which said humidifier unit locates in use, said humidifier unit substantially enclosed within said compartment, said compartment including a heater base, said assisted breathing unit further including an inlet vent open to atmosphere on said outer casing, a blower inlet port, a single gases path running between said inlet vent and said blower inlet port, and a means to provide a pressurised gases stream along said gases path, in use said blower inlet port and said humidifier gases inlet port in gaseous communication, said gases stream entering said humidifier unit via said humidifier gases inlet port and exiting said humidifier unit via said humidifier gases outlet port, a connection means to provide said gases stream exiting said humidifier unit to a patient interface, a lid unit, said lid unit adapted to close and seal said top fill aperture of said humidifier unit and to connect with said outer casing to hold said humidifier unit rigidly in position relative to said assisted breathing unit in use.

In a fourth aspect, the invention may broadly be said to consist in a humidifier unit adapted for use in conjunction with an assisted breathing unit that includes a heater plate, said humidifier unit comprising;

a humidifier chamber that includes said top fill aperture, and a heater plate that is adapted to contact said heater base in use, the wall of said chamber having a gases inlet and a gases outlet, an elongate inlet passage extending into said humidifier chamber from said gases inlet, said entry passage including a first opening in that end of said entry passage spaced from the wall of said chamber, an elongate exit passage extending into said humidifier chamber from said gases outlet, said exit passage including a second opening in that end of said exit passage spaced from the wall of said chamber, said first and second openings aligned to face substantially vertically upwards, a baffle means located between said first and second openings and adapted to prevent air entering said chamber from said inlet passage from directly entering said exit passage.

In a fifth aspect, the invention may broadly be said to consist in an assisted breathing unit comprising;

an outer casing including a humidifier compartment into which a humidifier unit can locate in use, said compartment sized and shaped to substantially enclose said chamber, said compartment including a heater base, said assisted breathing unit further including an inlet vent open to atmosphere on said outer casing, a blower inlet port, a single gases path running between said inlet vent and said blower inlet port, and a means to provide a pressurised gases stream along said gases path, in use said blower inlet port in gaseous communication with a humidifier gases inlet port, a connection means to provide said gases stream exiting said humidifier unit to a patient interface, means for receiving and releasably engaging a lid unit that is adapted to hold said humidifier chamber in position in said compartment.

In a sixth aspect, the invention may broadly be said to consist in an assisted breathing unit comprising;

an outer casing including a humidifier compartment into which a humidifier unit can locate in use, said compartment sized and shaped to substantially enclose said chamber, said compartment including a heater base, said assisted breathing unit further including an inlet vent open to atmosphere on said outer casing, a blower inlet port, a gases path running between said inlet vent and said blower inlet port, and a means to provide a pressurised gases stream along said gases path, in use said blower inlet port in gaseous communication with a humidifier gases inlet port, a connection means to provide said gases stream exiting said humidifier unit to a patient interface, means for receiving and releasably engaging a lid unit that is adapted to hold said humidifier chamber in position in said compartment.

In a seventh aspect, the invention may broadly be said to consist in an integrated blower/humidification system for providing heated humidified gases to a user, comprising:

a humidifier unit adapted to contain a volume of water and also adapted for use in conjunction with a heater base such that said volume of water can be heated, said humidifier unit having a gases inlet port and a gases outlet port, an assisted breathing unit having an outer casing and including a humidifier compartment into which said humidifier unit locates in use, said humidifier unit substantially enclosed within said compartment, said compartment including a heater base, said assisted breathing unit further including an inlet vent open to atmosphere on said outer casing, a blower inlet port, a gases path running between said inlet vent and said blower inlet port, and a means to provide a pressurized gases stream along said gases path, in use said blower inlet port and said humidifier gases inlet port in gaseous communication, said gases stream entering said humidifier unit via said humidifier gases inlet port and exiting said humidifier unit via said humidifier gases outlet port, a connection means to provide said gases stream exiting said humidifier unit to a patient interface, said breathing unit, said compartment and said gases path shaped and aligned to minimise the volume of said breathing unit.

In an eighth aspect, the invention may broadly be said to consist in an integrated blower/humidification system for providing heated humidified gases to a user, comprising:

a humidifier unit adapted to contain a volume of water and also adapted for use in conjunction with a heater base such that said volume of water can be heated, said humidifier unit having a gases inlet port, a gases outlet port and a top fill aperture, an assisted breathing unit having an outer casing and including a humidifier compartment into which said humidifier unit locates in use, said humidifier unit substantially enclosed within said compartment, said compartment including a heater base, said assisted breathing unit further including an inlet vent open to atmosphere on said outer casing, a blower inlet port, a gases path running between said inlet vent and said blower inlet port, and a means to provide a pressurized gases stream along said gases path, in use said blower inlet port and said humidifier gases inlet port in gaseous communication, said gases stream entering said humidifier unit via said humidifier gases inlet port and exiting said humidifier unit via said humidifier gases outlet port, a connection means to provide said gases stream exiting said humidifier unit to a patient interface, a lid unit, said lid unit adapted to close and seal said top fill aperture of said humidifier unit and to connect with said outer casing to hold said humidifier unit rigidly in position relative to said assisted breathing unit in use.

In a ninth aspect, the present invention broadly consists in a control knob assembly that is operable by a user to generate control signals, comprising:

a mounting plate including a recess, below which associated detector magnetic components are situated;

an operable control knob that is securable within the aperture of the mounting plate, the control knob having:

a button that is resiliently depressible by a user between a rest position and an operative position, the button being biased toward the rest position and having an associated magnetic component(s) that is arranged to move with the button; and a boss that surrounds the button and that is rotatable either clockwise or anticlockwise about the button by a user, the boss having an associated magnetic component(s) that is arranged to rotate with the boss; and control circuitry that is arranged to detect depression of the button and/or rotation of the boss by sensing magnetic field fluctuations caused by interaction of the magnetic components of the button and/or boss with the detector magnetic components situated below the mounting plate to generate control signals representing operation of the button and/or boss by a user.

In a tenth aspect, the invention may broadly be said to consist in a control system for an integrated assisted breathing and humidifier unit, said control system comprising;

a controller including controller memory, said controller controlling the operation of said integrated assisted breathing and humidifier unit;

a display panel controlled by said controller; and a user options selector, said controller responsive to changes in said options selector.

In an eleventh aspect, the invention may broadly be said to consist in a method for altering the control settings of an integrated assisted breathing and humidifier unit having a controller controlling the operation of said integrated assisted breathing and humidifier unit, said method comprising the steps of:

detecting the rotational position of a rotatable user options selector;

displaying, the currently selected option, based on the rotational position of said rotatable selector; and detecting movement of said user options selector along the axis of rotation of said selector, in response to said movement moving to a option chosen mode for the selected option.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The term 'comprising' as used in this specification means 'consisting at least in part of', that is to say when interpreting statements in this specification which include that term, the features, prefaced by that term in each statement, all need to be present but other features can also be present.

BRIEF DESCRIPTION OF THE DRAWINGS

A preferred form of the present invention will now be described with reference to the accompanying drawings.

FIG. 13b shows a cross sectional view along the line A-A of the humidifier chamber, humidifier chamber lid and locking handle of FIG. 13a.

DETAILED DESCRIPTION OF THE PREFERRED EMBODIMENT

Figure 1:
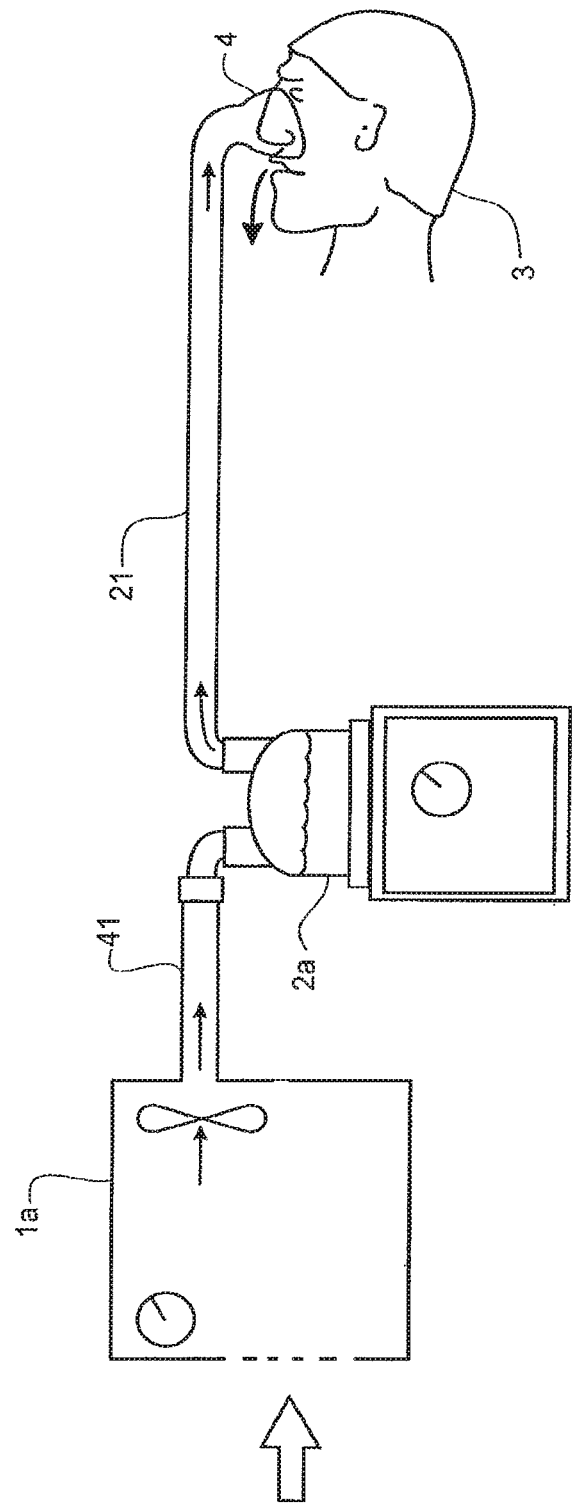
FIG. 1 shows a schematic view of a user receiving humidified air from a modular blower/humidifier system of a known, prior art, type.

A schematic view of a user 3a receiving air from a known (prior art) modular assisted breathing unit and humidifier system is shown in FIG. 1. Pressurised air is provided from an assisted breathing unit or blower 1a via a conduit 41 to a humidifier chamber 2a. Humidified, heated and pressurised gases exit the humidifier chamber 2a via a conduit 21, and are provided to the patient or user 3 via a user interface 4. The user interface 4 shown in FIG. 1 is a nasal mask, covering the nose of the user 3. However, it should be noted that in systems of these types, a full face mask, nasal cannula, tracheostomy fitting, or any other suitable user interface could be substituted for the nasal mask shown.

Figure 2:
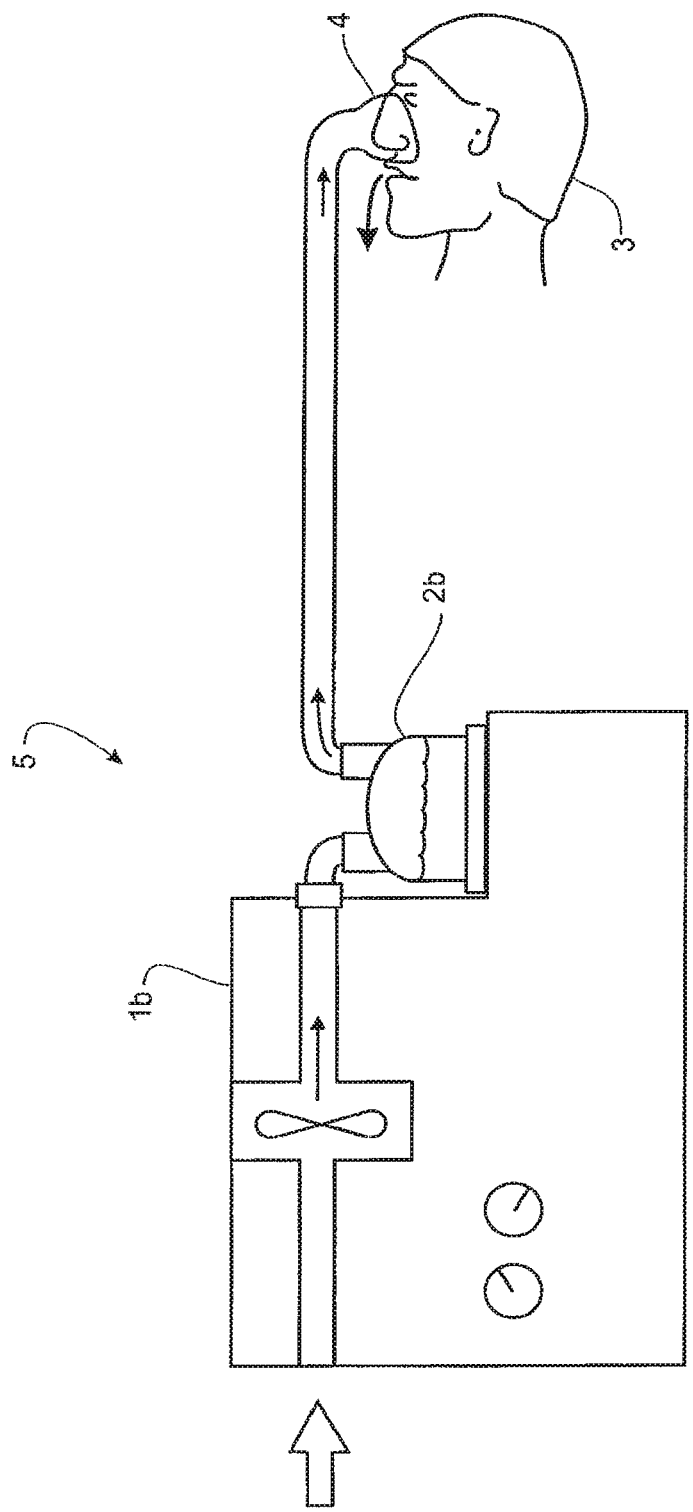
FIG. 2 shows a schematic view of a user receiving humidified air from an integrated blower/humidifier system of a known, prior art, type.

A schematic view of the user 3 receiving air from a known, prior art integrated blower/humidifier unit 5 is shown in FIG. 2. The system operates in the same manner as the modular system shown in FIG. 1, except that humidifier chamber 2b has been integrated with the blower unit 1b to form the integrated unit 5.

The integrated blower/humidifier unit 6 of the present invention can be substituted for the unit 5 of FIG. 2. The preferred form of the integrated blower/humidifier unit 6 is shown assembled and ready for use in FIG. 3. The unit 6 has two main parts: An integrated assisted breathing unit 7 (also known as a blower unit), having an outer shell which forms part of the breathing unit 7 and also encloses the working parts of the assisted breathing unit—e.g. the fan, internal-ducting and the internal control system; and a humidification unit 31 (described in detail below).

Assisted Breathing Unit

The preferred form of assisted breathing unit or integrated unit 6 will now be described with reference to FIGS. 4-17.

Figure 4:
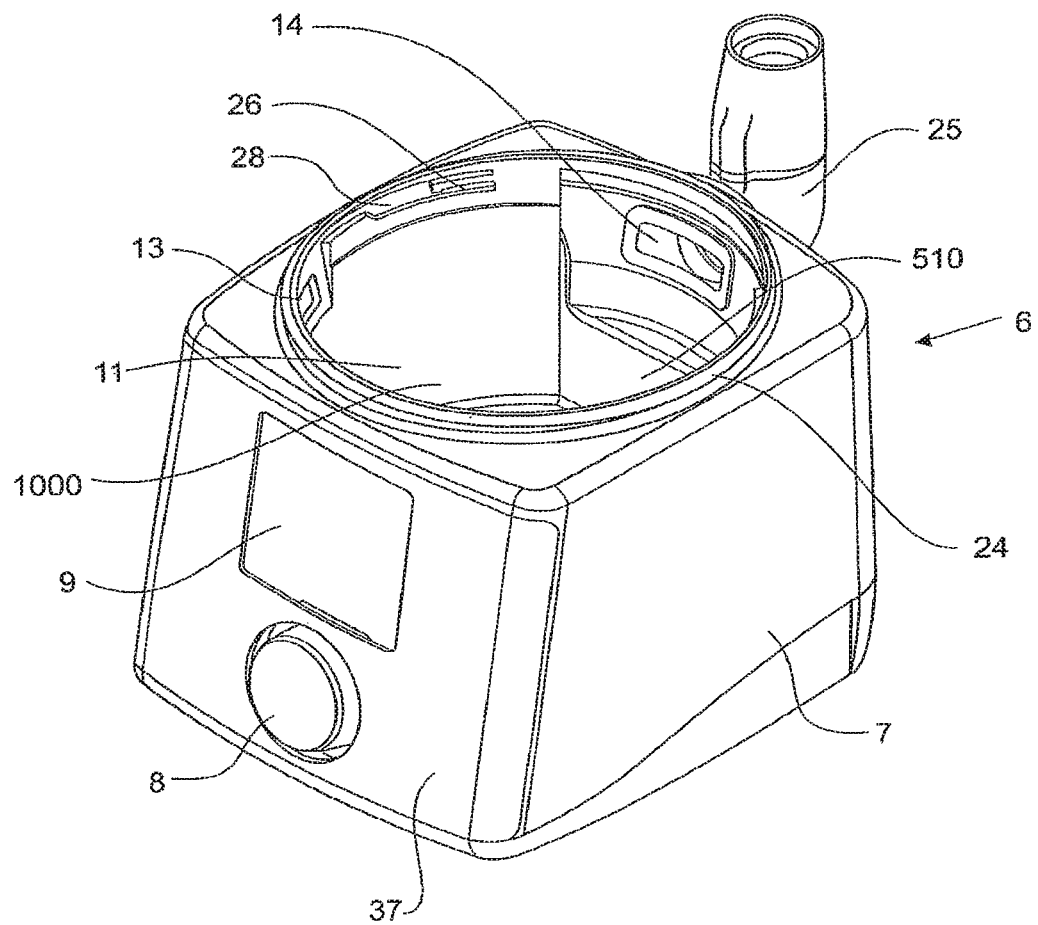
FIG. 4 shows a perspective view of the blower unit of FIG. 3, with the humidifier unit removed (not shown).

The integrated unit 6 consists of two main parts: an assisted breathing or blower unit 7 and a humidification unit 31. The humidification unit 31 is enclosed within the external casing of the integrated unit 6 in use, except for the top part. The structure of the humidification unit 31 is described in greater detail below. The blower unit 7 has an outer shell which is a generally rectangular block with substantially vertical side and rear walls, and a front face that is angled slightly rearwards. In the preferred embodiment, the walls, base and top surface are all manufactured and connected as far as possible to minimise the occurrence of seams, and any necessary seams are sealed. This outer shell encloses the working parts of the blower unit 7, and forms part of the blower unit 7. As shown in FIG. 4, a control knob 8 is located on the lower section of the front face of the integrated unit 6, with a control display 9 located directly above the knob 8. A patient outlet 25 is shown passing out of the rear wall of the integrated unit 6. In the preferred embodiment, in use the free end of the outlet 25 faces upwards for ease of connection. However, the preferred form of patient outlet 25 can be rotated to one side or the other to move or align it in a more convenient position for storage ox for a more convenient use position. The patient outlet 25 can include an elbow. The patient outlet 25 is adapted to allow both pneumatic and electrical connection to one end of a conduit—e.g. conduit 21—running between the unit 6 and a patient interface—e.g. interface 4. An example of the type of connector that can be used and the type of dual connection that can be made is described in U.S. Pat. No. 6,953,354. It should be noted that for the purposes of reading this specification, the patient interface can be thought of as including both the interface 4 and the conduit 21 where it would be appropriate to read it in this manner.

Figure 3:
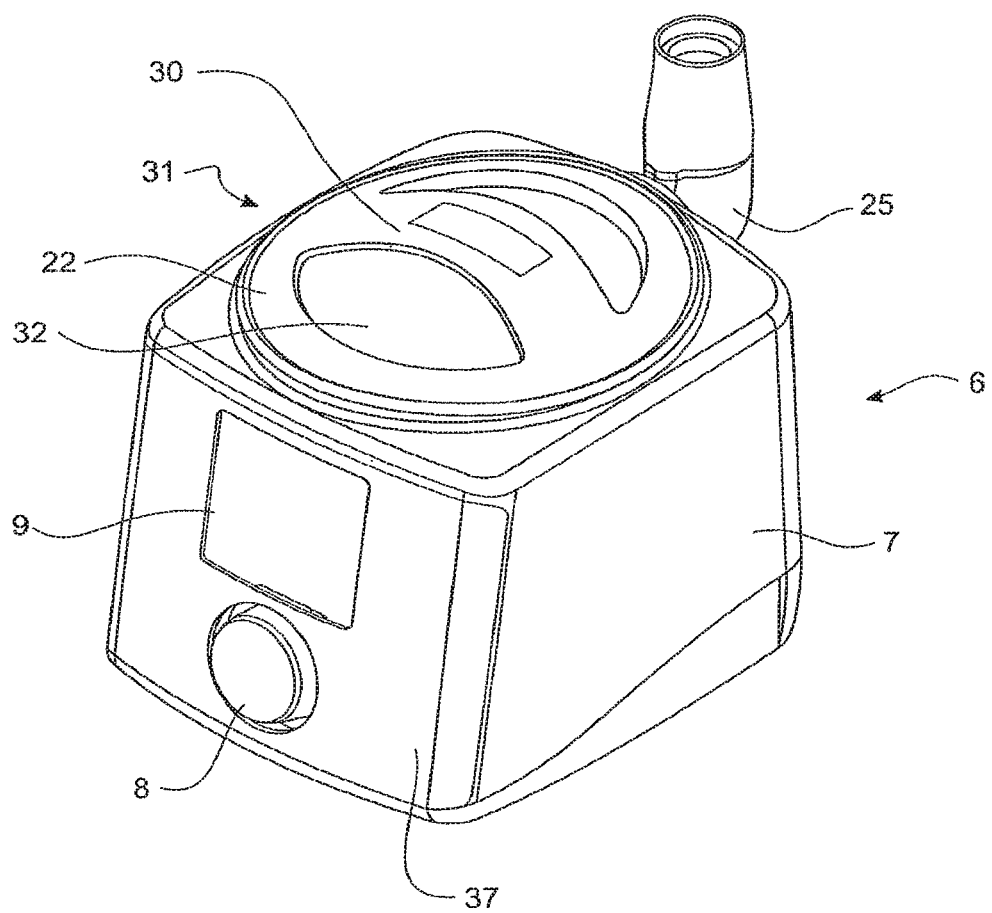
FIG. 3 shows a perspective view of the preferred embodiment of the integrated blower/humidifier of the present invention, which has a separate humidifier chamber and assisted breathing unit that are shown with the humidifier chamber in place within the blower unit ready for use.

In FIG. 3, a locking handle 22 is shown in position on the top surface of the integrated unit 6. The locking handle 22 is a separate item that can be unlocked and removed from the remainder of the integrated unit 6. The locking handle 22 includes a grip 30, adapted to act as a handle to allow a user to lift and carry the integrated unit 6, and also adapted to enable the handle 22 to be rotated from a locked position to an unlocked position. The locking handle 22 can be releasably locked to the remainder of the integrated unit 6. The function of the locking handle 22 will be more fully described below in the 'humidifier unit' section.

FIG. 4 shows the integrated unit 6 with the locking handle 22 removed and the humidification unit 31 not shown. That is, just the blower unit 7 is shown. The top surface of the blower unit 7 includes a circular humidifier aperture 1000, leading to an internal humidifier compartment 11. The opening includes a rim 24 located around the circumference of the opening. In use, a humidifier chamber 12 is located within the compartment 11. The humidifier chamber 12 will be described in detail below. The humidifier chamber 12 is in use fully enclosed inside the compartment 11, except for the uppermost part. When the chamber 12 is described as enclosed in the blower unit 7, it can be taken to mean fully enclosed except for the uppermost portion, as well as fully enclosed including the uppermost portion.

Figure 5B:
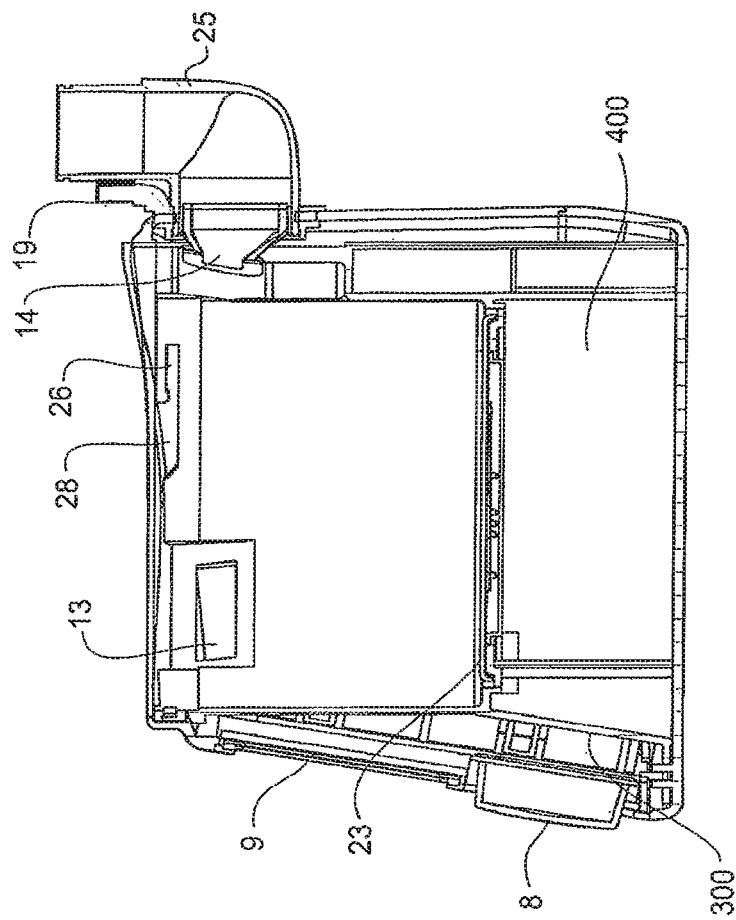
FIG. 5b shows a cross-sectional view along section line D-D of the blower unit of FIG. 4.
Figure 5A:
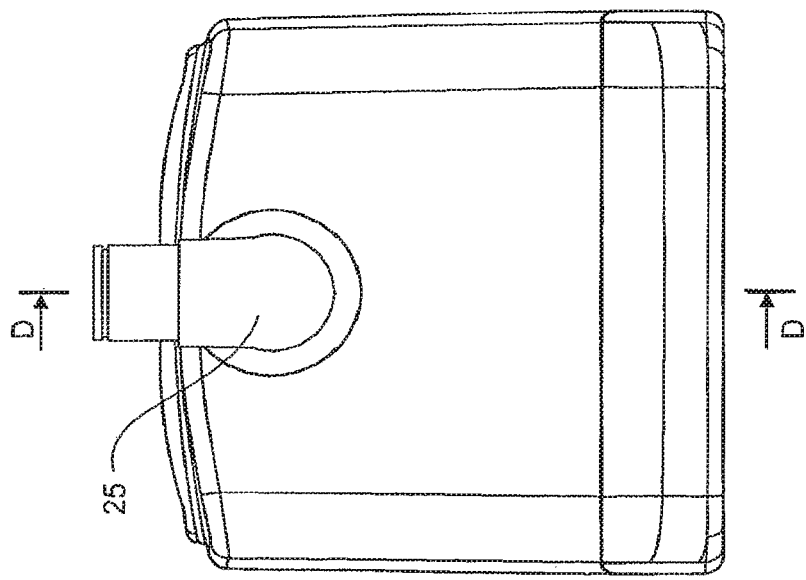
FIG. 5a shows a rear view of the blower unit of FIG. 3, with a section line D-D shown.

The internal structure of the blower unit 7 will now be described with reference to FIGS. 4 and 5. A heater base 23 is located at the bottom of the compartment 11. The heater base 23 is mounted to the floor of the compartment 11 in such a way that it has a small amount of elastic or compression resilience. That is, it can be pushed downwards a short distance within the compartment, but will push back against any downwards force that is applied. In the absence of any downwards force it will return to its initial position. This can be achieved by spring loading the base 23, or by any other of the methods that are known in the associated arts. A blower inlet port 13 and blower outlet port 14 are located on the wall of the compartment 11, towards the top of the compartment 11. In the preferred embodiment, these blower ports 13, 14 are aligned so as to mate with humidifier ports 15, 16 located on the humidifier chamber 12 in use (described in detail below) so as to form a blower-to-humidifier gases route which allows gases to exit the blower 7 and enter the humidifier chamber 12. It should be noted that other forms of blower inlet are possible. For example a conduit running between the blower unit 7 and e.g. the lid of the humidifier chamber 12.

Figure 7:
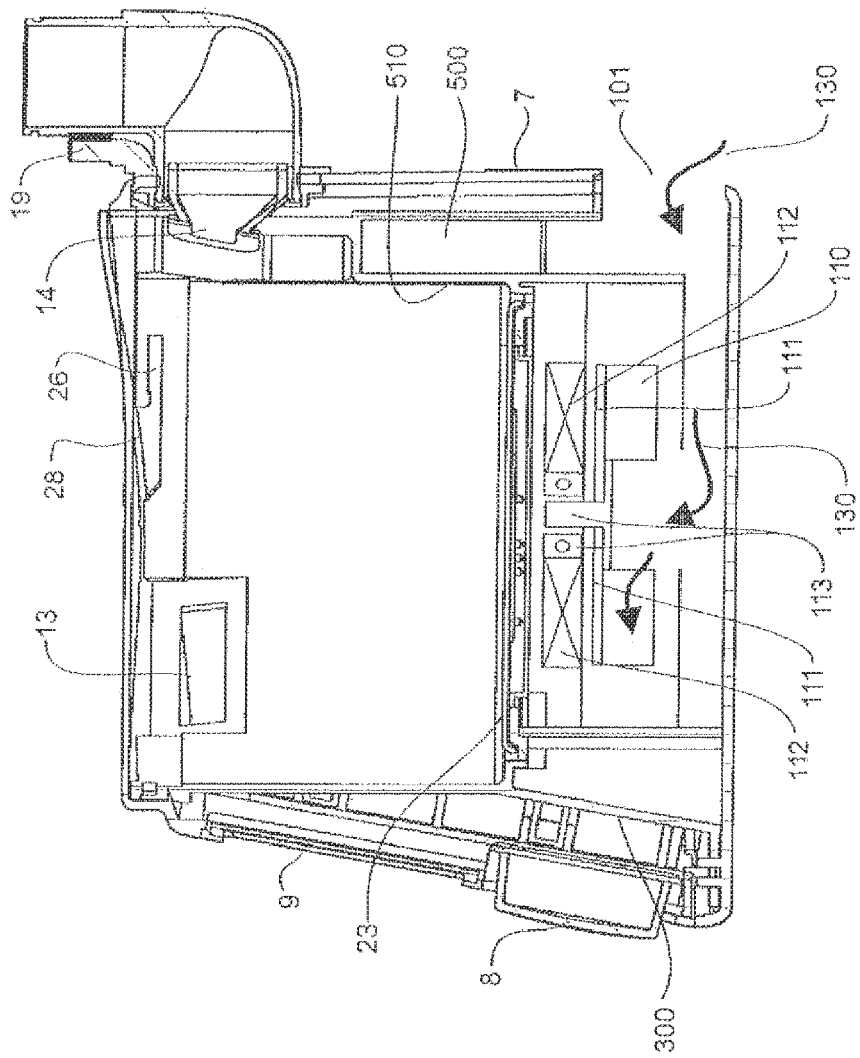
FIG. 7 shows a schematic detail view along section line DD of the internal structure of the blower unit.
Figure 8:
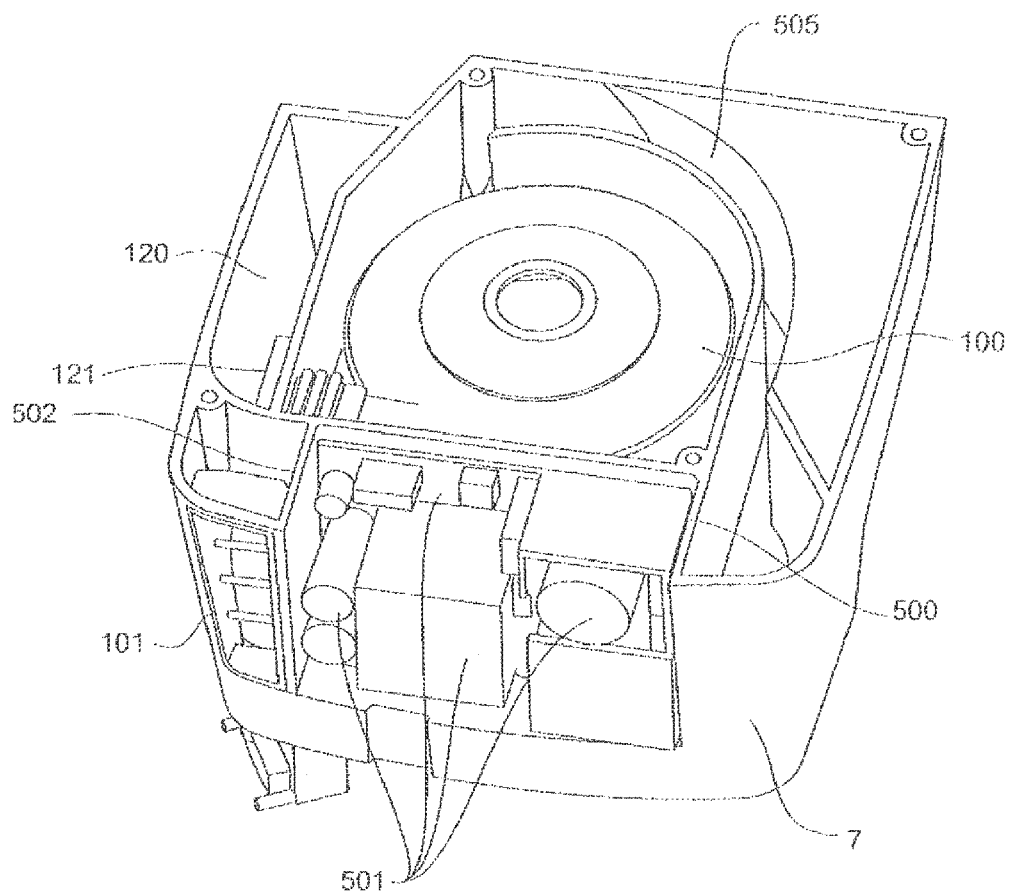
FIG. 8 shows a cutaway view of the blower unit from underneath and to the rear looking forwards, with detail of an air inlet duct, a power supply and power supply sub-housing, a fan, and an air path through the unit shown.
Figure 9:
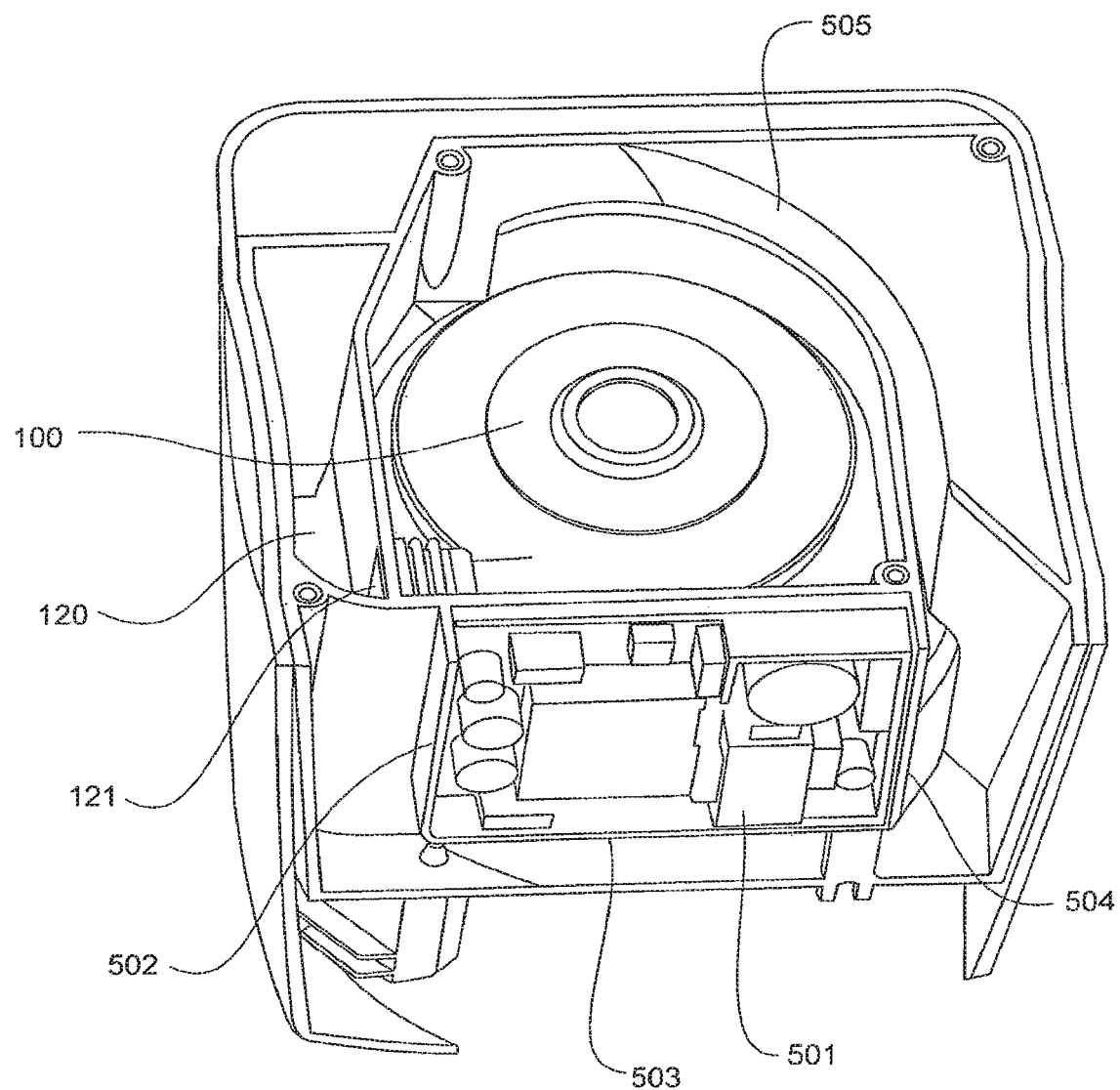
FIG. 9 shows a cutaway view of the blower unit from underneath and to the rear looking forwards, with the rearmost part of the blower unit cut away to show detail of the air path around the power supply sub-housing.
Figure 10A:
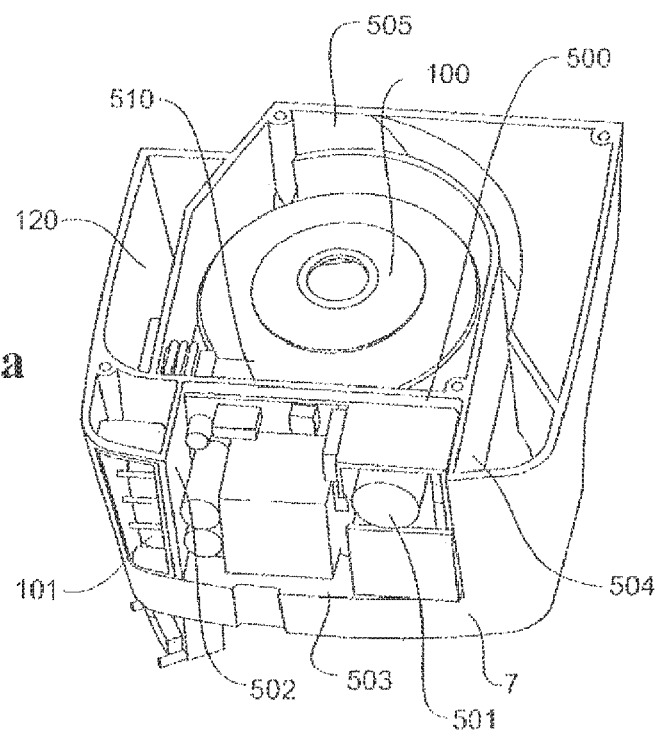
FIGS. 10a and 10b show cutaway views of the blower unit from underneath and to the rear looking forwards, with FIG. 10a showing the blower unit with the base and part of the rear wall removed, and FIG. 10b showing the rear part of the blower cutaway further forward than the view of FIG. 10a, to show detail of the air path over the power supply sub-housing.
Figure 10B:
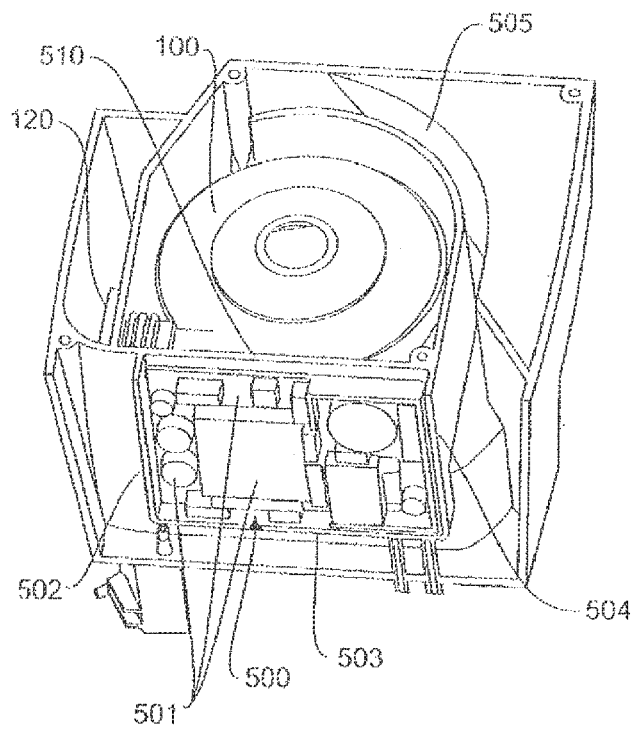
Figure 11A:
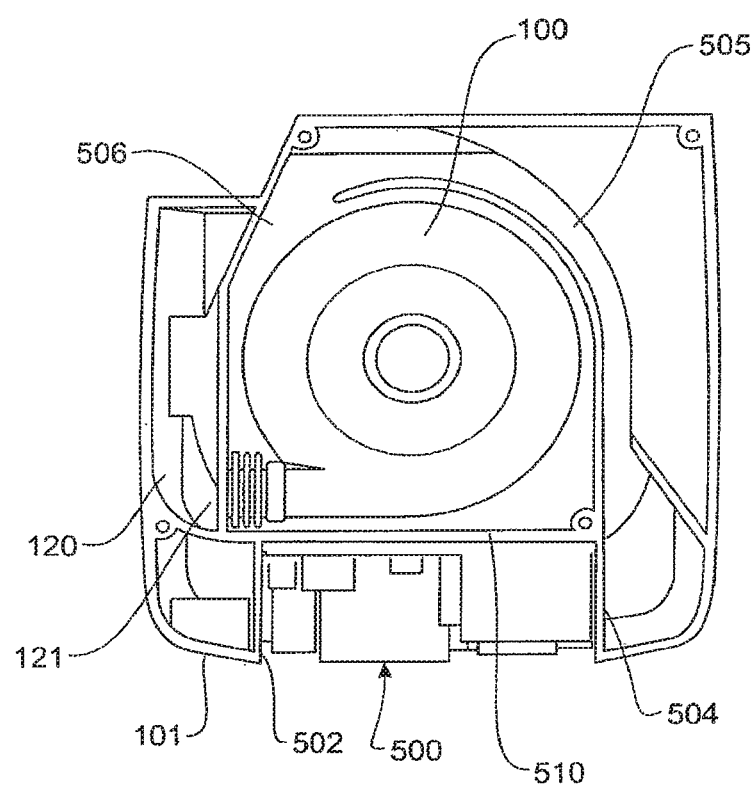
FIG. 11a shows a cutaway bottom view of the blower unit of the preceding Figures, with the base removed.
Figure 11B:
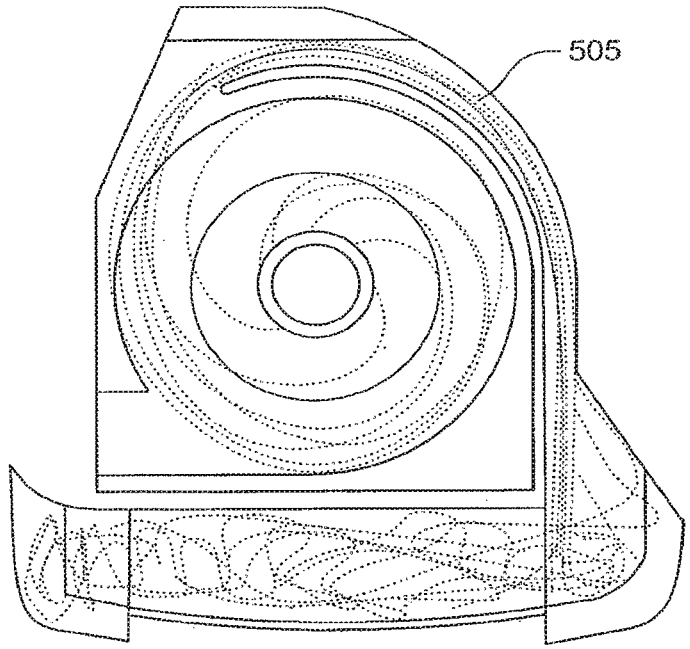
FIG. 11b shows a schematic view of the blower of FIG. 11a, with the air path and turbulence shown as the air passes firstly into the air inlet duct, then over and around the power supply sub-housing, and then into and out of the fan.
Figure 12:
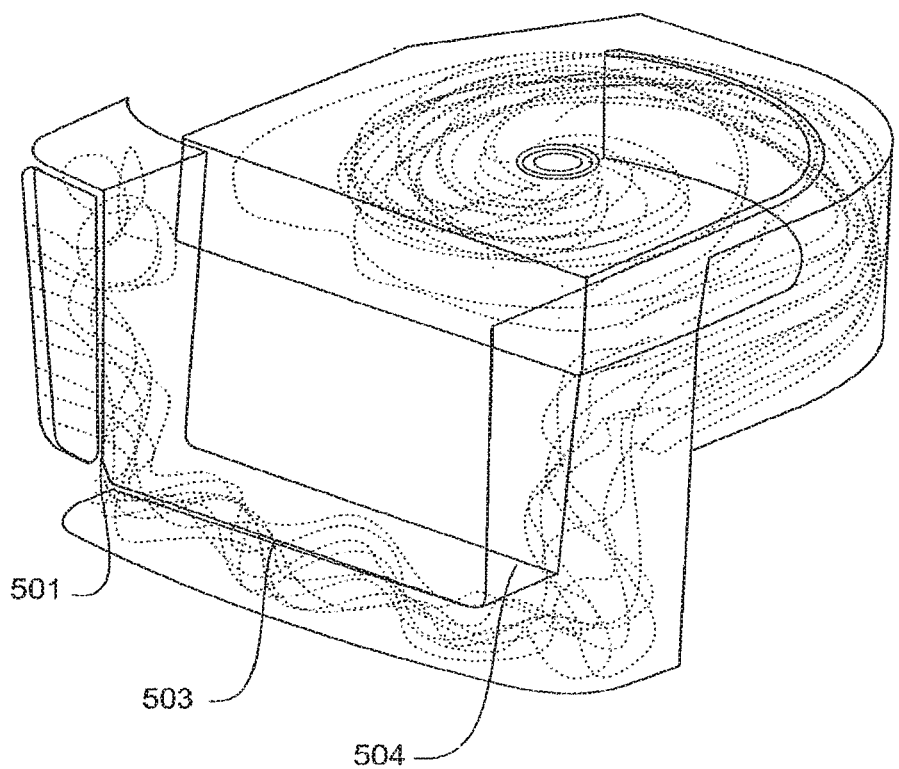
FIG. 12 shows a schematic line view of the blower unit underneath and to the rear looking forwards, with the air path and turbulence shown as the air passes firstly into the air inlet duct, then over and around the power supply sub-housing, and then into and out of the fan.

As shown in FIGS. 7 and 8, the integrated unit 6 includes an inlet vent 101 to draw air in from atmosphere. The integrated unit 6 also includes a mechanism for providing a pressurised air flow from the inlet vent 101 to the humidifier chamber. This vent 101 can be located wherever is convenient on the external surface of the integrated unit 6. In the preferred embodiment, as shown in FIG. 8, it is located on the rear face of the blower unit 7. In the preferred embodiment, air is drawn in through the vent 101 by a fan unit 100 which acts as the preferred form of pressured air flow mechanism (described in detail below). The air is inducted or otherwise directed through the casing to the inlet port 13. In use, air will exit the main body of the blower unit 7 via the inlet port 13 and then enter the humidifier chamber 12, where it is humidified and heated, before passing out of the chamber 12 through the outlet port 14, which is directly connected to the patient outlet 25. The heated humidified gas is then passed to the user 3 via e.g. a conduit 21. The patient outlet 25 is adapted to enable pneumatic attachment of the patient conduit 21, and in the preferred embodiment, electrical connection at the outlet 25 is also enabled via an electrical connector 19. A combined electrical and pneumatic connection can be useful for example if the conduit 21 is to be heated. Electrical heating of a conduit such as conduit 21 can prevent or minimise the occurrence of condensation within the conduit 21. It should also be noted that the outlet connection does not have to be via the housing of the integrated unit 6. If required, the connection for the conduit 21 could be located directly on an outlet from humidifier chamber 12. The preferred form and variations can generally be referred to as connection mechanisms.

Figure 6:
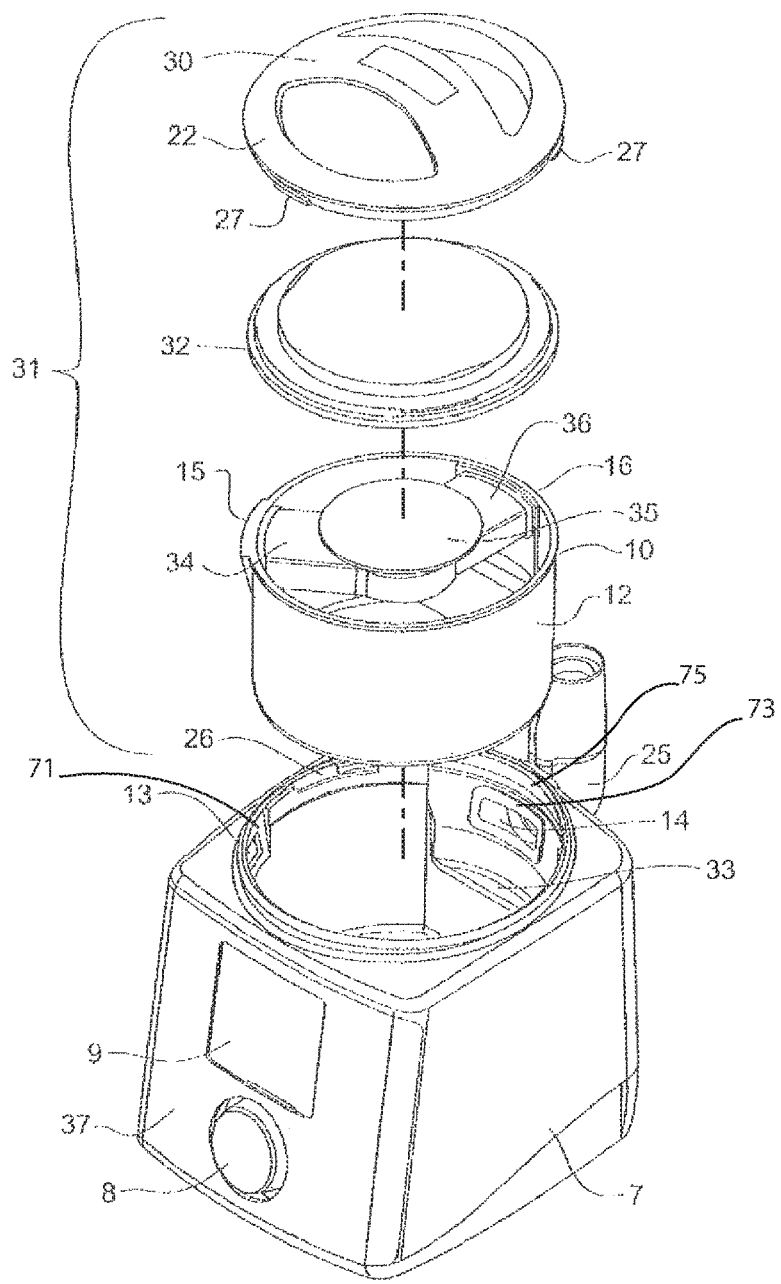
FIG. 6 shows an exploded view of the blower unit and the humidifier unit of FIG. 3.

As shown in FIGS. 6 and 7, the inlet port 13 is offset. That is, the port is positioned facing into or out of the corner of the integrated unit 6 between the side wall and the front face. In contrast, outlet port 14 is directly aligned with the rear wall of the integrated unit 6. It can also be seen from FIG. 6 that the circular compartment 11 is sized to just fit within the generally square plan view profile of the integrated unit 6. Offsetting the inlet port 13 towards the corner allows a more efficient use of the space within the assisted breathing integrated unit 6, and allows the size of the integrated blower/humidifier unit 6 to be minimised.

The locking handle 22 and the integrated unit 6 include a locking mechanism for locking the handle 22 to the integrated unit 6. In the preferred embodiment the locking mechanism is as follows: the rim 24 includes two mating grooves 26 located just below the rim 24, spaced opposite each other on the circumference of the rim 24. More than two of the mating grooves 26 can be used if required. The grooves 26 correspond to an equal number of mating lugs 27 on the locking handle 22. The mating groove or grooves 26 have an entry point 28 on the rim 24, with the main part of the groove 26 located slightly below the rim 24. The lugs 27 are pushed downwards into the entry points 28, and the handle is rotated so that the lugs enter the main part of the grooves 26 to hold the handle 22 in place. Different locking mechanisms can be used if required.

Humidifier Chamber with Lid

Figure 17:
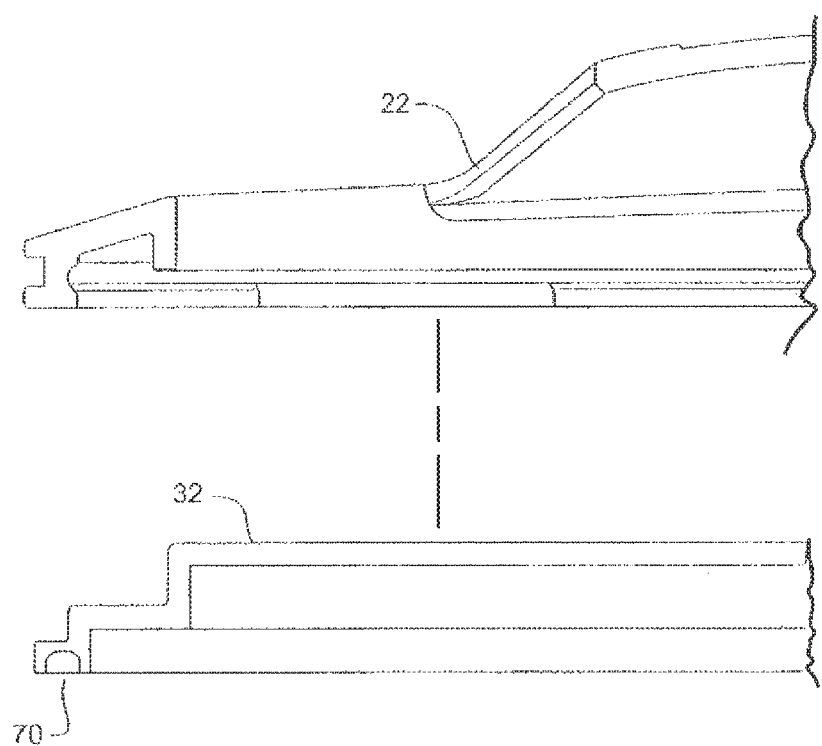
FIG. 17 shows a partial view of the lid of FIG. 6, and a locking handle used to hold the lid in position, with the lid and locking handle separated.

The humidifier unit 31 will now be described in more detail with particular reference to FIGS. 13 and 17.

In the preferred embodiment, the humidifier unit 31 is comprised of three main parts: humidifier chamber 12, lid 32 and locking handle 22 (counted as part of the humidifier unit for the purpose of describing the operation of the integrated unit 6).

Figure 13B:
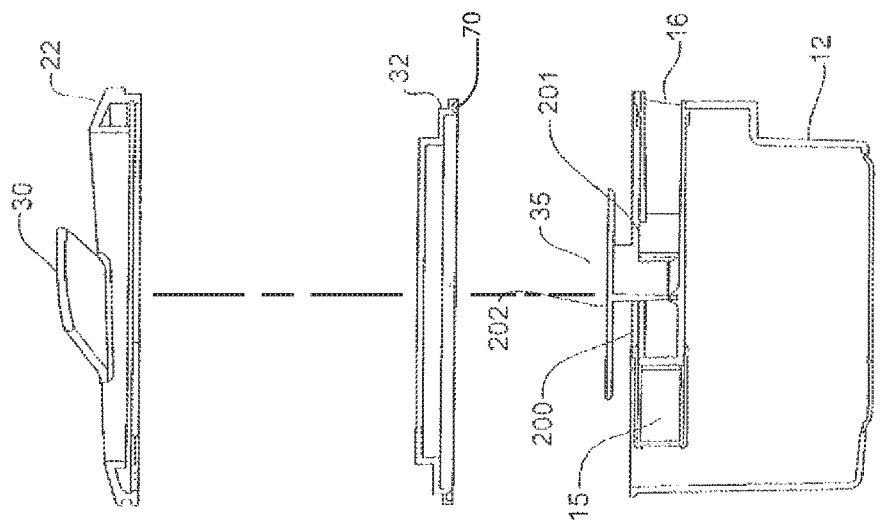
Figure 13A:
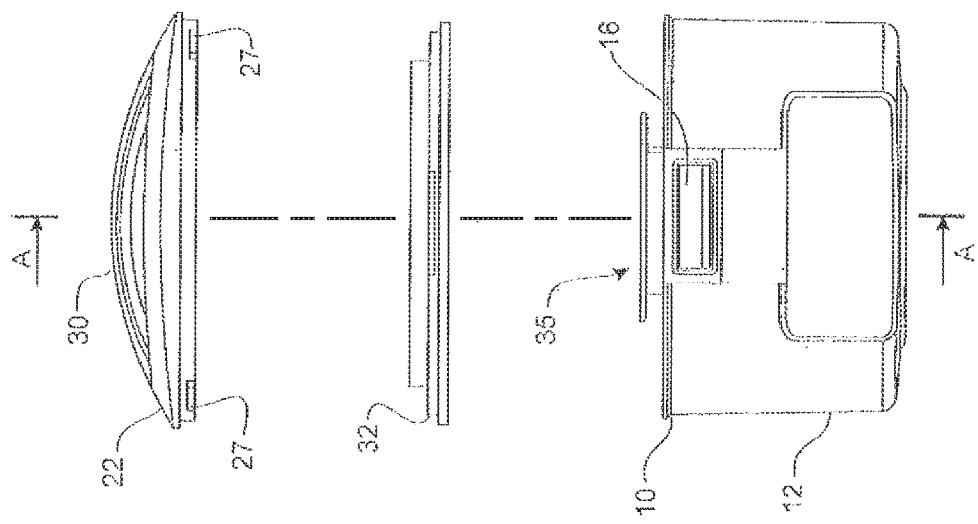
FIG. 13a shows a rear view of the humidifier chamber of the present invention, with a humidifier chamber lid and a locking handle shown in exploded view above the humidifier chamber, and a section line A-A shown.

The preferred embodiment of the humidifier chamber 12 is an open-topped container, with a heat conducting base. The chamber 12 is sized to fit snugly within the compartment 11 on the integrated unit 6. That is, the chamber 12 is enclosed within the blower unit except for the open top of the chamber 12. A fully open topped chamber 12 is the preferred form. However, an alternative form of the chamber 12 could have a closed top surface, and would include an opening on the chamber (not necessarily on the top surface), sized appropriately so that a user can easily fill the chamber 12. The preferred form of chamber 12 with an open top, and the alternative form that includes a fill opening on the top are referred to as 'open top', or 'top openings' within this specification. The open top may also be referred to as a 'top fill aperture'. It should also be noted that when the humidifier chamber 12 is referred to as 'enclosed', or 'substantially enclosed' in relation to the integrated breathing assistance apparatus, this has the meanings defined above. The chamber 12 is generally circular, but the lower part of the rear (relative to the integrated unit 6) is flattened as shown in FIGS. 13a and 13b to correspond to a ledge 33 on the lower rear side of the compartment 11. This ensures that the chamber 12 will always be oriented correctly in use. It should be understood that other methods of achieving the same result could also be used. For example, the chamber 12 and integrated unit 6 could include complimentary grooves and slots. The chamber 12 can also include features such as a fill or level line if required. The humidifier inlet port 15 and a humidifier outlet port 16 are located in the wall of the humidifier chamber 12, towards the top of the chamber wall These are positioned so as to align with the blower inlet and outlet ports 13 and 14 when the humidifier chamber 12 is in position, forming the blower-to-humidifier gases route as described above. It is preferred that the corresponding ports on the blower 7 and humidifier chamber 12 are shaped so as to minimise airgaps. A good seal is preferred but not required. In the preferred form, the rim or perimeter of the chamber 12 includes a chamber seal 10, formed from soft silicone or similar. When the chamber 12 is placed in position in the humidifier compartment 11, the chamber seal 10 is pressed against the wall or walls of the compartment 11, and the body of the chamber 12 and the seal 10 ensure that the chamber 12 is sealed, so that air exiting the blower through the port 13 cannot escape to atmosphere. This helps ensure that a pressurised airstream enters the humidifier chamber 12 in use. If required, a substantially unbroken ring of sealing material such as soft silicone can be added to the wall of the compartment 11 at or close to the upper rim of the chamber 12, to form a compartment seal (not shown) instead of or as well as the chamber seal 10. In alternative embodiments the ports 13, 14 are surrounded by resilient sealing gaskets such as silicone gaskets to assist in forming a seal in use. If preferred, the resilient sealing gaskets around the ports can be used as well as the compartment and/or chamber seals.

Air enters the humidifier chamber 12 through the humidifier inlet port 15, and passes along a generally horizontal entry passage 34 towards the centre of the humidifier chamber 12. Passage 34 is offset towards one of the front corners of the unit to align with the inlet port 13 as described above. The air exits the entry passage 34 through a first aperture or opening 200 in the centre of the humidifier chamber 12 aligned facing upwards (that is, in the top of the passage). The air is then directed into the main part of the chamber by a baffle 35. In cross section, the baffle 35 is T-shaped, with a vertical central portion to deflect gases entering the chamber 12, and a substantially horizontal top 'umbrella' portion 202, which is circular in plan view, as shown in FIGS. 6 and 13. Air is deflected by the baffle 35 as it exits the passage 34, and then enters the main part of the chamber 12 where it is heated and humidified. The heated and humidified gases then enter an exit passage 36 on the other side of the baffle 35 through a second aperture or opening 201, with the air passing through the exit passage 36 to the chamber exit port 16 and then into the breathing unit outlet port 14, and on to the user 4 as described above. It can be seen that the baffle 35 prevents air from the inlet passage 34 from directly entering the exit passage 36 before it has been heated and humidified. The passage and baffle arrangement also serves the purpose of acting as a splash baffle as well as an air baffle. Water is obstructed from entering the passages 34 and 36 if the chamber 12 is tilted while it contains water. The umbrella portion 202 of the baffle 35 acts as a shield for the passages 34, 36, vertically occluding the apertures 200, 201, so that when a user is pouring or refilling the chamber 12, the user cannot directly pour into either of the apertures 200, 201. The top surface of the passages 34, 36 also acts as a shield to prevent a user pouring water into the passages 34, 36. It is preferred that the exit and entry apertures 200, 201 in the passages 34, 36 face upwards, as this helps to prevent water or liquid in the chamber splashing into the passages 34, 36, or otherwise entering the passages 34,36 when the chamber 12 is tilted.

The passages, 34, 36 and the baffle 35 can be generally referred to as the baffle, or the baffle mechanism.

In use, the chamber 12 is positioned (in the correct orientation) within the compartment 11. The lid 32 is then placed on top of the chamber 12. The lid 32 is sized so that it will pass through the top opening of the integrated unit 6, with the lower surface of the lid 32, close to the edge, sealing onto the upper edge of the chamber 12. In the preferred embodiment, the lid 32 has an. edge perimeter portion that is aligned facing downwards. This has a central recess that is filled with a silicone seal 70 or similar which is pressed onto the upwards facing edge of the chamber 12 when the lid 32 is in position. This arrangement is shown in FIG. 13. In FIG. 13 the handle 22 is also shown vertically above the lid 32 (separate from the lid 32). The lid 32 is sized to fit into the recess shown in the handle 22 (if the handle shown in FIG. 13 is pressed vertically downwards onto the lid 32). If required, the two contacting portions of the lid 32 and the chamber 12 can also be shaped to improve the seal between the two. The central part of the lid 32 is bulged upwards so that it will stand proud of the baffle 35. The lid 32 is placed in position on the chamber 12 once the chamber 12 has been filled. The locking handle 22 is then positioned above the lid 32. As has been described above, lugs 27 on the circumference of the locking handle 22 engage with complimentary grooves 26 on the rim 24. In order to engage correctly, it is necessary in the preferred embodiment for the locking handle 22 to be pressed or pushed downwards, pushing both the lid 32 and the chamber 12 downwards onto the heater plate. The heater plate will give slightly under the downwards pressure, allowing the locking handle 22 to be rotated so that the lugs 27 engage with the grooves or slots 26. Once the downwards force is removed, the chamber 12, lid 32, and locking handle 22 will be pressed upwards by the reaction force from the heater plate, with the assembly held in place by the lugs 27 and slots 26. In the preferred embodiment, the slots 26 are shaped so that the locking handle 22 cannot be rotated to disengage the lugs 27 without pressing the locking handle 22 downwards slightly first. The locking handle 22 also includes the grip 30, which in the preferred embodiment is an arched member passing from one side of the handle 22 to the other, sized and shaped so that a user can pass at least some of their fingers underneath, so as to manipulate the locking handle 22 and to carry the integrated unit 6 if necessary. In the preferred embodiment, the locking handle 22 and the lid 32 are separate items, as described. If the handle 22 is used without the lid 32, the chamber will not be sealed, and the heated, humidified air will escape or vent to atmosphere before entering the exit port 14. Any air that does enter the port 14 will be at a lower pressure than required, due to the leaking. To ensure correct operation, the lid must be used to seal the chamber in the preferred embodiment. This ensure that there is less chance of incorrect use of the unit. For example, if a user fills the compartment 11 directly without using the chamber 12, or if a user forgets to place the lid 32 in position.

In the preferred form, the top portion of the lid 32 fits into a central recess in the handle 22, as can best be seen in FIG. 6b. The lid 32 and the handle 22 are sized so that the lid 22 will snap-fit and be held in place in the handle 22 to form an integrated lid unit. The lid 22 can be disengaged from the handle 32 by pressing on its top surface or similar. However, it is preferred that the snap-fit will keep them engaged in normal usage. £\s the handle recess and the lid 22 are circular, they can easily rotate relative to one another when engaged. When the handle 22 is rotated to disengage it from the integrated unit 6, it will rotate easily relative to the lid 32

(which will not rotate easily due to the seal on the perimeter edge). When the handle 22 has been disengaged from the integrated unit 6, it can be lifted away from the integrated unit 6 to remove both the handle 22 and the lid 32.

It should be noted that although a round chamber 12, lid 32 and a locking mechanism (lugs 27 and slots 26) have been described, and locking/unlocking of the lid 32 is achieved by rotating the separate locking handle 22, this is not the only way in which this effect can be achieved. If a different locking mechanism is used in place of the lugs 27 and grooves 26, chambers with different profiles can be used in place of the round chamber 12 described above. For example, spring loaded clips could be used, with the clips released by a button placed in a convenient location, such as on a handle or on the outer surface of the integrated unit 6. A hinged lid could also be used, with a clip and complimentary catch located on the lid and the blower unit, to hold the lid closed in use. Alternatively or as well as, the chamber lid 32 and the locking handle 22 could be integrated as a single unit. This single unit could either be separable from the integrated unit 6 or the humidifier unit 31, or an integral part of it, for example a hinged lid similar to that suggested above. The intention of the lid 32 and handle 22 in the arrangement described above is that a user can easily remove the lid 32 in order to access the chamber 12 for refilling or similar, and that a user can then easily replace the lid 32 and handle 22 to hold the lid 32 and the chamber 12 in position inside the assisted breathing integrated unit 6.

It should be noted that as outlined above, use of a round chamber 12, with a generally square profile integrated unit 6 allows an efficient use of space so that the overall size of the integrated unit 6 can be minimised. This should be considered if using an alternative layout or locking mechanism.

Control Knob

Figure 14:
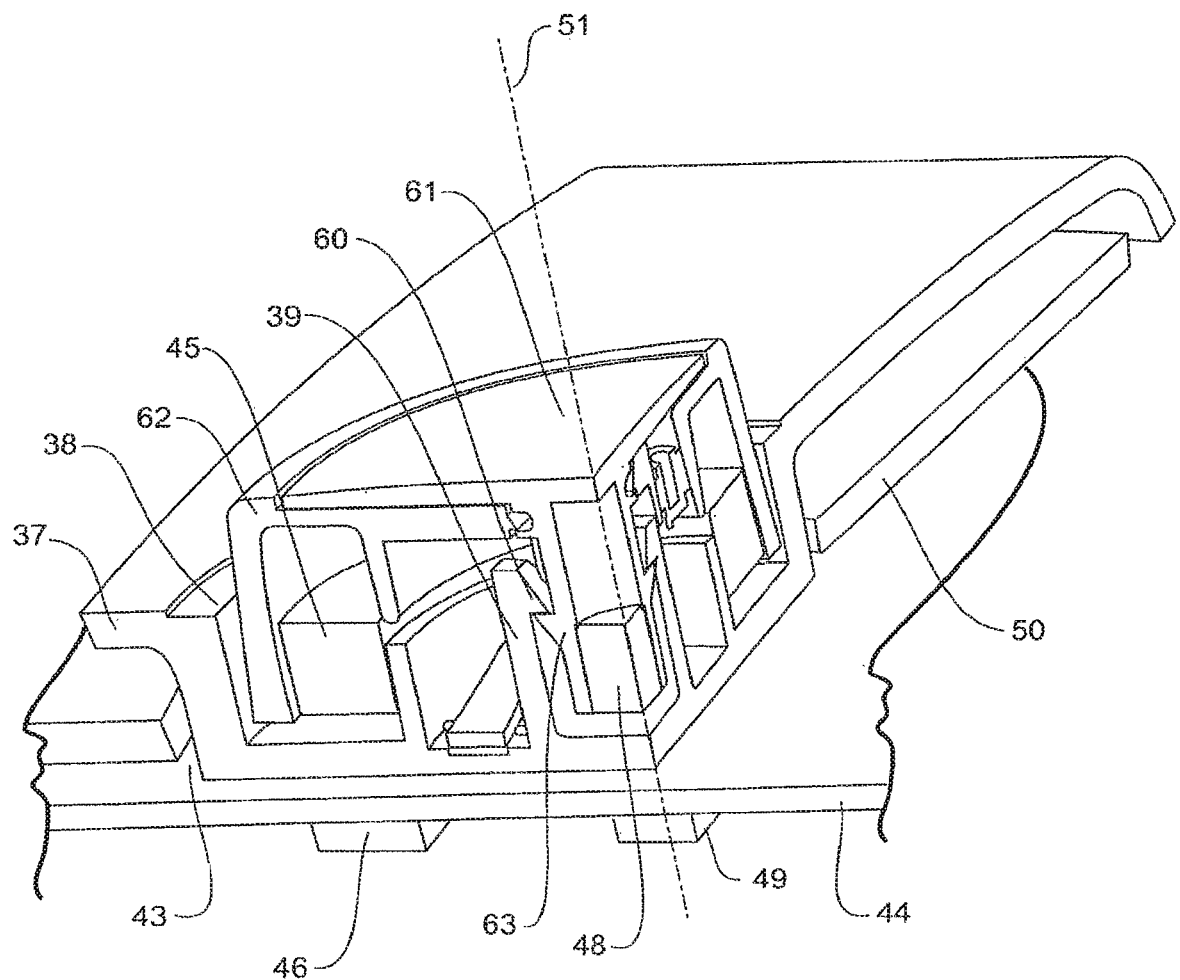
FIG. 14 shows a schematic cross-section of part of the front of the blower unit.

The preferred form of construction of the control knob assembly including operable control knob 8, and attachment to the integrated unit 6 will now be described with particular reference to FIG. 14. The knob 8 is manipulable by a user to change the settings of the integrated unit. This is achieved by twisting and pushing the knob 8 to generate control signals.

In the preferred embodiment, the integrated unit 6 includes a removable mounting plate removable faceplate 37 that removably attaches onto the front face of the integrated unit 6—e.g. by friction-fit push clips or similar, sufficient to hold the faceplate 37 in place in use or during transport, but allowing the faceplate 37 to be removed e.g. by pressing a knife blade under one side and twisting or similar. The faceplate 37 includes an aperture that aligns with the control screen 9, so that the screen can be viewed through the aperture in use. FIG. 14 shows a schematic cross-section of the front surface of the integrated unit 6, viewed from above. For clarity, the various elements shown in FIG. 8 are shown not in contact with one another. As shown in FIG. 14, the face plate 37 includes a concave hollow, depression or recess 38, into which the knob 8 locates in use. The depression 38 is sized and shaped so that the knob 8 fits snugly. The bottom of the depression 38 contains a fastening mechanism 39. In the preferred embodiment, the fastening mechanism 39 is formed as an integral part of the plate 37. In the preferred embodiment, the fastening mechanism 39 is a ring or crown of spring fasteners or fastening clips 39, with their tips or upper portions 60 facing or pointing inwards. The fastening clips 39 are aligned perpendicular to the base of the depression 38. The knob 8 is made up of a central, non-rotating portion or button 61 and an outer, rotatable portion or boss 62 that can be rotated either clockwise or anticlockwise by a user. The outer portion 62 is ring-shaped, with a central aperture. The inner portion 61 has a T-shape in cross-section, with fasteners 63 integral with the upright of the T. In use, the fasteners 63 connect with the sprung fasteners 39 to hold the inner portion in position. The knob assembly is assembled by placing the outer (rotatable) portion 62 of the knob 8 in position in the depression 38, and then pushing the inner (non-rotatable) portion 61 into position. The flat upper part of the inner portion acts as a flange to hold the outer portion 62 in position. In the preferred embodiment, the outer portion 62 also has a slight central hollow, with the cross-portion of the T-section of the inner portion 62 fitting snugly into this hollow so that the inner portion 61 and the outer portion 62 together form a flush outer surface.

What has been described above is the preferred form of fastening mechanism to hold the knob 8 in position on the faceplate 37. However, any suitable fastening mechanism could be substituted for the one described.

The knob 8, or more specifically the outer portion 62, is fitted with a ring magnet 45. The outer portion 62 generally has the form of a hollow cup, with the open face facing inwards towards the centre of the depression 38 in use. The ring magnet 45 is fitted running around the inside of the outer portion, just below the rim. The centre of the ring magnet 45 is aligned with the axis of rotation of the knob 8. As the outer portion 62 rotates, the ring magnet 45 also rotates.

The front face or wall 50 of the assisted breathing or integrated unit 6 is located behind the faceplate 37. The front face 50 includes an aperture 43, through which the rearmost part of the depression or recess 38 passes in use. A connector board 44 is located just behind, and generally planar with, both the faceplate 37 and the front face 50 of the integrated unit 6. Magnetic or magnetised sections 46 are embedded on the inner surface of the connector board 44. These are positioned to as to form a generally circular shape, corresponding to the ring magnet 45, so that the magnetised sections 46 align with the ring magnet 45. The magnetic fields of the ring magnet 45 and the magnetised sections 46 (detector magnetic components, or boss detector magnetic components) interact as the knob is rotated in use. Control circuitry and sensors (not shown) located within the blower unit 6 are connected to the ring magnet 45 so that as the boss portion 62 of the knob 8 is turned it can detect the fluctuations of the interacting magnetic fields. In the preferred form, the ring magnet 45 is continuous (that is, a continuous annular component), but divided into a number of discrete magnetic sections (That is, there are no physical gaps between the sections). The number of sections' can be varied depending on the number of positions required. One advantage of using a ring magnet such as ring magnet 45 is that is has discrete sections. This means that as the boss portion of the knob 8 is rotated, it will have a number of discrete positions, having preferred 'rest' positions as the fields of the magnetised sections 46 and the fields of the sections of the ring magnet 45 interact to reach an equilibrium point, an effect known as 'cogging'. The outer portion 62 of the knob 8 will rest at these equilibrium points until acted on by an external force—e.g. a user exerting a rotational force on the rotatable outer portion 62 of knob 8. The knob 8 will therefore tend to naturally 'jump' from one rest position to the next as it is rotated. As the relative positions of the magnets 45 and 46 changes, the fluctuations of the relative magnetic fields changes is detected by the sensors, and the results of the fluctuations are passed to the control circuitry 300 located inside the housing of the respirator 7 (e.g.

located on the circuit board 44), which alters the output parameters of the integrated unit 6 according to pre-programmed responses (e.g. altering the power to the heater base 23, fan speed, etc) as required by a user.

The preferred form of ring magnet 45 and magnetised sections 46 has been described above. It should be noted that the positions of the ring magnet 45 and magnetised sections 46 could be reversed. Also, the ring magnet 45 could be composed of discrete sections, with gaps between them. That is, an annular arrangement of individual magnetic components. Magnetised sections 46 have been described. These could be actual magnets, or alternatively these could be electromagnetised elements that act both as magnets and sensors to exert a cogging force and provide positioning feedback.

In the preferred embodiment, the knob 8 is also adapted to allow limited movement along its axis of rotation 51. That is, it can be pressed inwards to act as a button. This can be achieved in a number of ways. However, in the preferred embodiment, a spring (not shown) is placed inside the circle or crown of the preferred form of fastening mechanism 39. When emplaced, this spring is slightly under compression, and pushes outwards against the knob 8 so that it has a rest position when not depressed and an operative position when depressed. When pressed inwards towards the integrated unit 6, the spring is compressed slightly more, and will act to return the knob 8 to its initial position once the pressing force is removed. The centre of the knob 8 also holds a magnet 48. A corresponding central magnet 49 (or button detector magnetic component) is located at the centre of the circle formed by sections 46. In a similar fashion to that described above, as the relative positions of the magnets 48 and 49 changes, the fluctuations of the relative magnetic fields are detected, and these changes are passed to a control unit which varies the output parameters of the integrated unit 6 accordingly. For example, using the arrangement described above, the knob 8 can be rotated clockwise and anticlockwise to scroll between menu options, and then pressed inwards to choose the option to which the user has scrolled. The knob 8 can also be used as e.g. an on/off switch, either by scrolling to the required on/off menu choice and pressing, or by pressing and holding the knob in for a longer period than would naturally occur if the unit 6 was accidentally knocked—for example 5 seconds. Alternatively, the controls could be set so that a user is required to pull the knob 8 slightly out from the unit 6 to turn it off.

What has been described above is an assembly where the medical device (blower unit 7) includes a faceplate 37 which includes a recess, and which fits over the front face 50 of the blower 7. The faceplate is unbroken, in that there are no apertures or gaps through which moisture or dirt can enter the medical device. Also, the components external to the blower 7 are not moisture or dirt sensitive, so if they get wet or dirty, their operational effectiveness is not adversely affected. It should be noted that what is described above is the preferred embodiment, and the principles of the operation could be applied equally well to a device which does not include a separate faceplate, and which has a single flat face (i.e. no recess), with magnetic elements 46, 63 located behind the face, and the control knob, boss, fastening mechanism, etc located external to the face. It should be noted that another possible variation of the layout described above could also be used, with the front face 50 unbroken and including a recess, and the faceplate including an aperture through which the control knob locates into the recess on the faceplate. It should also be noted that the faceplate does not have to present at all, but is present in the preferred forms.

Control Menu

Figure 15:
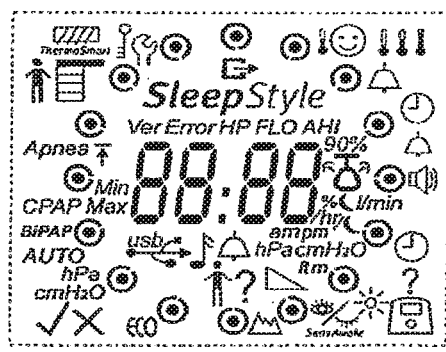
FIG. 15 shows a preferred form of main menu that is displayed on a display panel of the integrated blower/humidifier of FIG. 3.

The preferred form of display shown on the display panel 9 is shown in FIG. 15. In the preferred embodiment, the control menu as displayed on the display 9 is a single layer menu, in order to keep the operation of the unit 6 simple. In the preferred embodiment, the display is an LCD display, with a circular ring of options around the outside of the display. As the knob 8 is rotated, each of the options will light up in turn. When the knob is depressed, that option will be chosen. Once an option is chosen, for example 'output power', the level of this parameter can be adjusted by rotating the knob 8 clockwise and anti-clockwise. A user can then exit this submenu and return to the main menu by, for example, tapping the knob inwards or pulling it outwards. The control circuitry can be programmed as required. Other options can be pre-programmed as required. For example, pushing and holding in the knob 8 (or pulling it outwards and holding it out) could turn the unit off. It is preferred that the discrete positions (the 'cogging' positions) that the knob 8 reaches as it is rotated correspond to different menu options.

Blower Unit

The internal structure of the blower unit 7 will now be described with reference to FIGS. 5 and 7-11. In the preferred embodiment, heater base 23 is located at the bottom of the compartment 11, as described above. It should be noted that the blower unit and humidification chamber could be configured so that the volume of water within the humidifier chamber is heated e.g. through the side walls. That is, contact with a heater element or unit through a heat conducting surface on the side wall of the chamber, rather than on the base of the chamber. This configuration would achieve substantially the same effect. However, heating through the base is preferred for reasons of simplifying the chamber construction and overall operation of the heater/humidifier unit. When 'heater base' is referred to in this specification, it should be taken to mean heating through the base of the humidifier chamber, or alternatively the side walls.

As described above, the integrated unit 6 includes an inlet vent 101 to draw air in from atmosphere. The integrated unit 6 also includes a mechanism and structure by which a pressurised air flow is provided from the inlet vent 101 to the humidifier chamber. The vent 101 can be located wherever is convenient on the external surface of the integrated unit 6, but in the preferred embodiment, as shown in FIGS. 7 and 8, it is located on the rear face of the blower unit 7, on the right hand side of the rear face (right hand side when looking forwards). In the preferred embodiment, air is drawn in through the vent 101 by a fan unit 100 which provides a pressurised gases stream through the blower unit 7. The pressurised gases stream is ducted or otherwise directed from the inlet vent 101 through the casing to the humidifier inlet port 13. The air path and the ducting will be described in detail in the 'Fan Unit and Air Path' section below. In use, air exits the main body of the blower unit 7 via the inlet port 13 and enters the humidifier chamber 12, where it is humidified and heated, before passing out of the chamber 12 through the outlet port 14, which is directly connected to the patient outlet 25. The heated humidified gas is then passed to the user 3 via e.g. a conduit 21. The patient outlet 25 is adapted to enable pneumatic attachment of the patient conduit 21, and in the preferred embodiment, electrical connection at the outlet 25 is also enabled via an electrical connector 19.

As shown in FIGS. 4 and 6, the inlet port 13 is offset. That is, the port is positioned facing into or out of the corner of the integrated unit 6 between the side wall and the front face. In contrast, outlet port 14 is directly aligned with the rear wall of the integrated unit 6. It can also be seen that the circular compartment 11 is sized to just fit within the generally square plan view profile of the integrated unit 6. Offsetting the inlet port 13 towards the corner allows a more efficient use of the space within the assisted breathing integrated unit 6, and allows the size of the integrated blower/humidifier unit 6 to be minimised.

Fan Unit

The fan unit and ducting of the preferred embodiment will now be described with reference to FIGS. 5, 7-12 and 16. The fan unit 100 is intended to sit in the recess 400 shown in FIG. 5b. Air is drawn into the fan unit 100 through an inlet vent 101. Once inside the housing, the air is then is drawn upwards into the casing of the fan unit 100 through an aperture 110 in the centre of the casing of the fan unit 100, and is directed outwards through a duct 120 (shown schematically as hidden detail in FIG. 16) to the inlet 13. The duct 120 runs from the recess 400 up between the side wall and the front wall of the integrated unit 6. The air path through the fan unit is shown by arrows 130. In the preferred embodiment, fan unit 100 is electromagnetically powered, with magnetic segments 111 interacting with electromagnetic coils 112, located above the fan unit 100, as shown in FIG. 7. The fan 110 is held in place by a bearing unit 113 that includes a spindle for the fan 110.

Fan Unit and Air Path

The fan unit and ducting of the preferred embodiment will now be described with particular reference to FIGS. 8 to 12. A power supply sub-housing 500 is located within and integrated with the outer housing or outer shell of the breathing unit 7. The power supply sub-housing 500 is a rectangular cuboid structure at the rear of the blower unit 7, integrated as part of the rear wall 80 of the blower unit 7. The cuboid sub-housing 500 shares one of its two largest faces with the rear wall 80 of the blower unit 7 (although it should be noted that the outer dimensions of the sub-housing 500 are substantially less than the dimensions of the rear wall 80). The other large face 510 is common with the fan recess 400, and the humidifier aperture 1000. The sub-housing 500 is generally centrally located on the inner rear wall of the blower unit 7. Once the unit is assembled, the sub-housing 500 is substantially closed off from atmosphere and the rest of the internal volume of the outer shell of the blower unit 7, apart from small apertures necessary for external electrical connections or similar (not shown). The power supply component board 501 is comprised of electrical components connected to a mother board, and slotted into the space within the sub-housing 500 during assembly. It is not necessary to detail or individually number all of the components used to make up the power supply component board 501, as the make-up and variations of the construction of power supply boards is well-known in the art. However, it should be noted that these components generate heat during use, which cannot dissipate or vent to atmosphere due to the power supply being enclosed. This heat therefore builds up, potentially leading to less efficient operation. It is preferred that the sub-housing 500 is sealed or enclosed in the sub-housing 500 in this manner in order to protect the components of the power supply component board 501, so that dirt, moisture or similar cannot enter the sub-housing 500. However, the power supply component board could be merely located within the external casing or shell of the blower unit 7. It should be noted that when 'power supply' or 'power supply unit' are referred to in this specification, this means either the power supply sub-housing 500, the power supply component board 501, or both together.

In order to help reduce the temperature of the sub-housing 500 and the temperature of the components of the power supply component board 501 in the sub-housing 500, air from atmosphere is drawn into the housing by the fan unit 100 and then ducted directly over the power supply unit sub-housing 500 to cool the power supply component board 501. It is preferred that the air is ducted over the sub-housing 500 directly after it enters the outer housing of the integrated unit 6, as the air will be at its coolest at this point—direct from the atmosphere. In order to most effectively cool the power supply component board 501 and the sub-housing 500, the air is ducted over the greatest possible surface area of the sub-housing 500, while still maintaining the integrity and operation of the integrated unit 6, and still maintaining a practical compact and integrated design.

Figure 16:
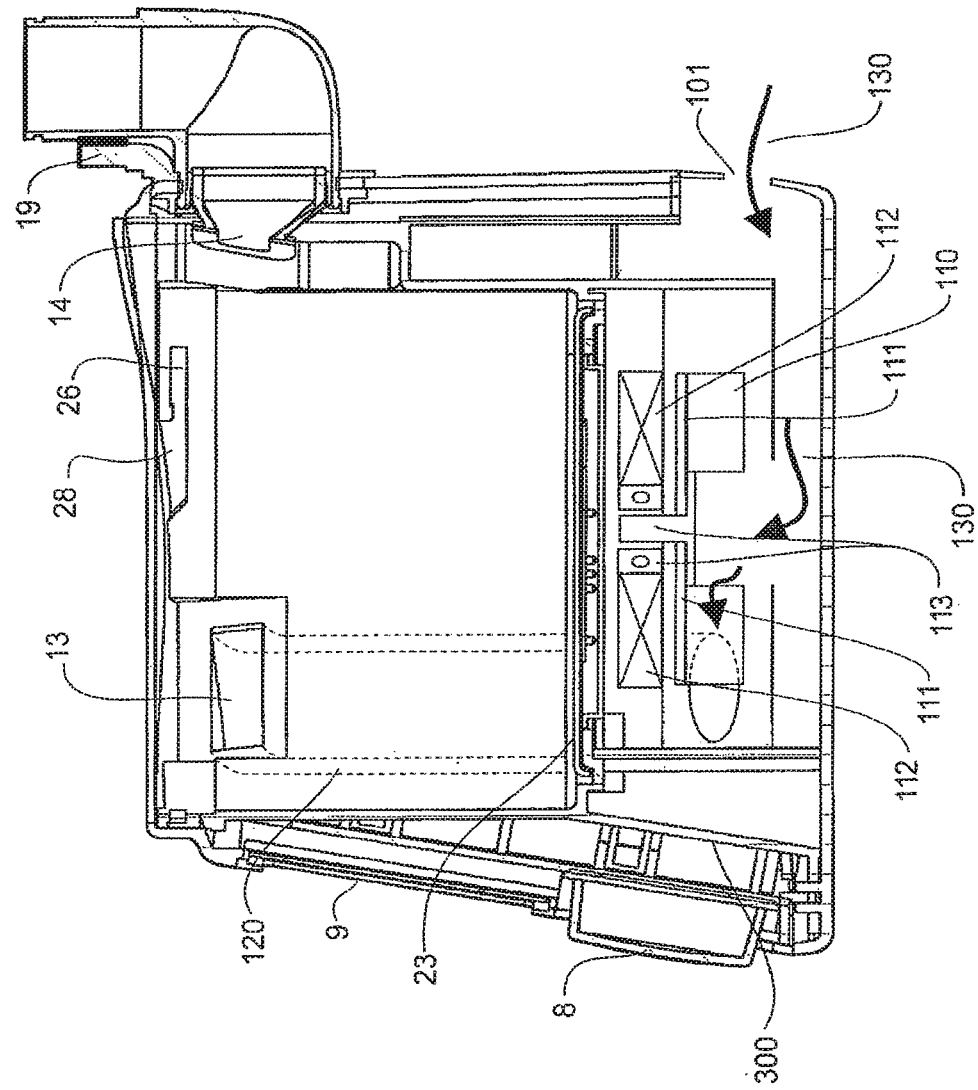
FIG. 16 shows a schematic view of the internal structure of the preferred form of fan and motor that can be used in the blower unit of FIG. 5b.

Air from atmosphere is drawn in through the air inlet vent 101, the side of which is substantially the same height as one of the sidewalls of the sub-housing 500. In the preferred embodiment, the inlet 101 is directly next to the sub-housing 500. It should also be noted that in the preferred form, the height of the air inlet 101 is substantially the same as the dimension of the neighbouring wall 502. The air entering the external shell through the inlet 101 therefore immediately contacts the side wall 502 of the sub-housing 500. This first contact is made across substantially the entire surface area of the wall, as the height dimension of the neighbouring vent 101 is substantially the same as the height or length of the wall 502. This has the advantage that all the air contacting this wall will be at atmospheric temperature as it contacts the wall. The air is then drawn by the fan 100 upwards and across the top wall 503 of the sub-housing 500, passing across or over the entire outer surface area of the top wall 503. The air is then ducted down the other, or inner side wall 504 of the sub-housing 500, passing across the entire outer surface area of wall 504. It should be noted that the walls of the sub-housing 500 are as thin as is practical in order to minimise their insulating effect, and maximise heat transfer between the air flow and the power supply board. The air is then drawn inwards, away from the power supply, along the curved path 505, through aperture 506 into the recess 400 and then into the fan unit 100. Air is drawn into the fan unit 100 through aperture 110, and is then directed outwards through a plenum chamber or duct 120 inside the blower 7 to the inlet 13 (duct 120 is shown schematically and for the purposes of illustration only as hidden detail in FIG. 16. The representation of the duct 120 as shown in FIG. 16 does not necessarily match the actual path or size of the duct). The duct 120 runs from the recess 400 up between the right side wall (from behind looking forwards) and the front wall of the integrated unit 6, up to the blower inlet port 13.

It can be seen that for an outer casing with a sub-housing 500 and air path configured in this manner, air passes over the entire surface area of three walls (502, 503, 504) of the sub-housing 500, substantially adding to the cooling of the power supply component board 501. This is the most preferred configuration of the cooling path, as manufacture in this configuration allows repeatability and a high number of units within design tolerance, while minimising costs. It has been found that this configuration gives the most efficient use of both space and air cooling, allowing a good degree of cooling, while still ensuring the unit 6 can be configured compactly to minimise footprint. It should be noted that if the power supply component board 501 is not enclosed in a sub-housing, the cooling air can be ducted directed over the board and the components thereon.

Other configurations are possible. For example, the air could be ducted along a space between the large wall 510 of the sub-housing 500, and the rear wall of the humidifier aperture 1000. However, in order to make this configuration work effectively, without the air in this space stagnating, the gap between the fan recess 400 and the power supply sub-housing 500 has to be over a certain size, and this can detract from the overall compact nature of the overall structure. Furthermore, it can add to the manufacturing difficulty. It should also be noted that the blower unit could be redesigned to allow the air path to pass over the lower wall of the sub-housing, as well as or instead of, the side and upper walls.

As described above, the sub-housing 500 is located at the rear of the blower unit 7. It could of course be located anywhere suitable, such as the sides or base, with the air ducting and inlet configured and located accordingly. The rear is preferred as this configuration allows the other elements of the blower unit to be configured to minimize the overall device 'footprint'.

In the most preferred form, the outer surfaces of the walls 502, 503 and 504 are ribbed, in order to increase the surface area available for cooling, and to aid in heat dissipation by acting in a similar manner to heat sinks. Also, in the most preferred form, air flows over at least two and preferably three walls of the sub-housing 500 in order to maximise the cooling.

Carry Case

As has been noted above, one problem that can occur when a user packs their breathing assistance apparatus in a case for travel is forgetting to empty the humidifier chamber, and the contents may then spill during travel, causing at least inconvenience. It is a long felt want by users of domestic breathing assistance apparatus that this problem is addressed.

In the preferred embodiment, a carry case 600 is used with the integrated unit 6 described above to help overcome this problem. When a user wishes to pack their breathing assistance device for transport, the carry case 600 can be used.

Figure 18:
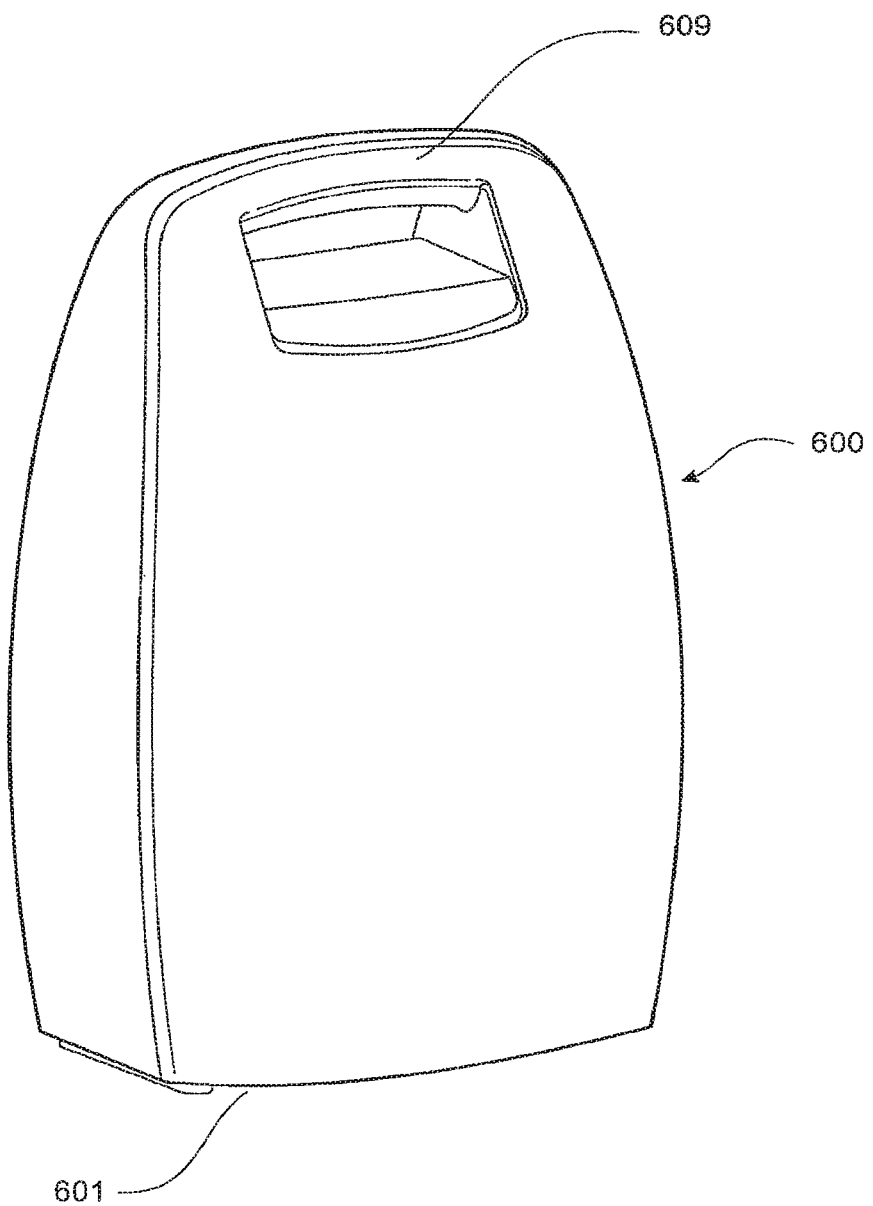
FIG. 18 shows a preferred form of carry case that can be used with the breathing assistance apparatus of the present invention, closed and upright resting on its end base.
Figure 19:
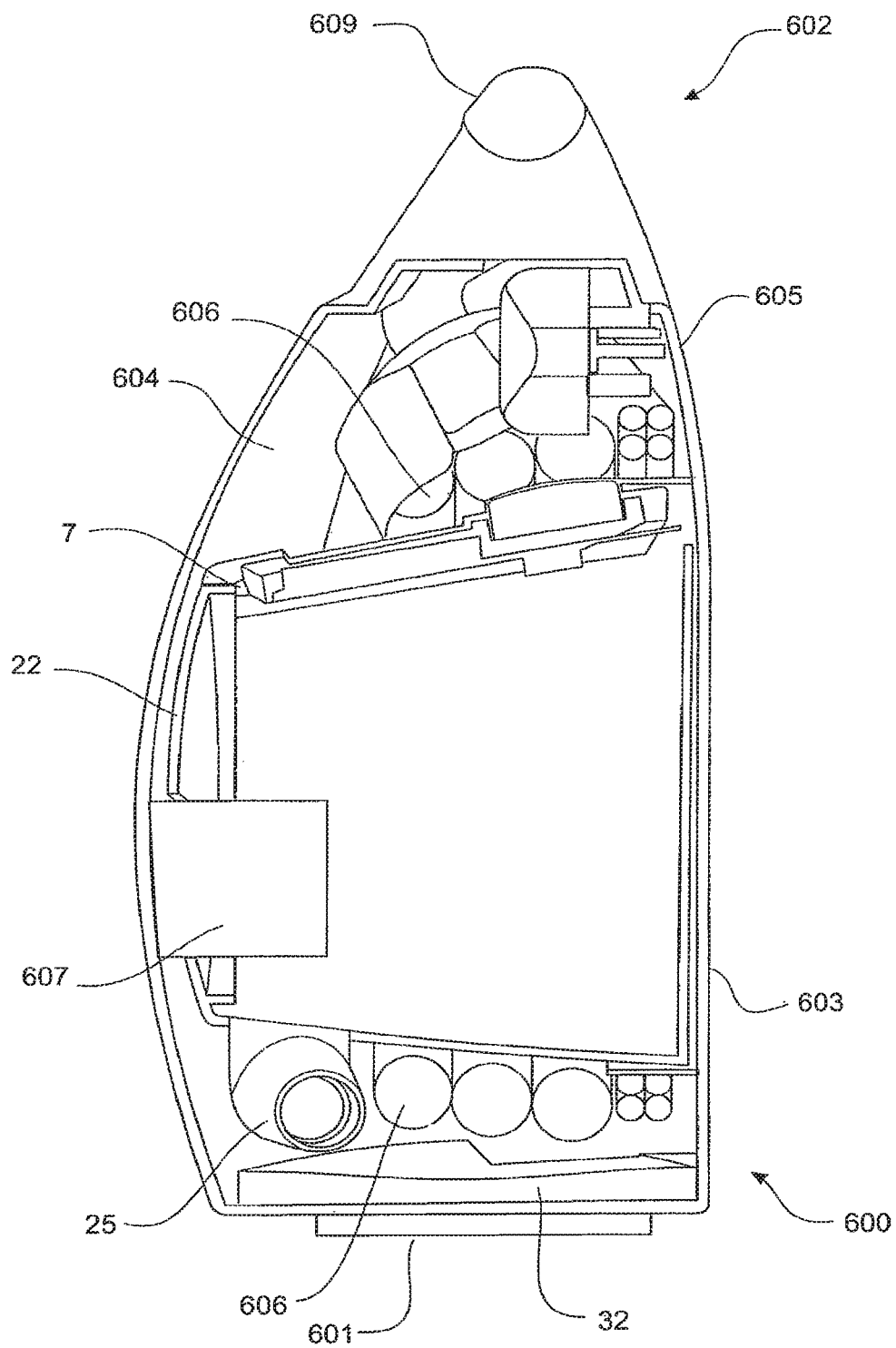
FIG. 19 shows a cutaway side view of the carry case of FIG. 18, resting on its side base, ready to be opened, with an integrated breathing assistance apparatus of the type shown in FIG. 3 located in the carry case.
Figure 20:
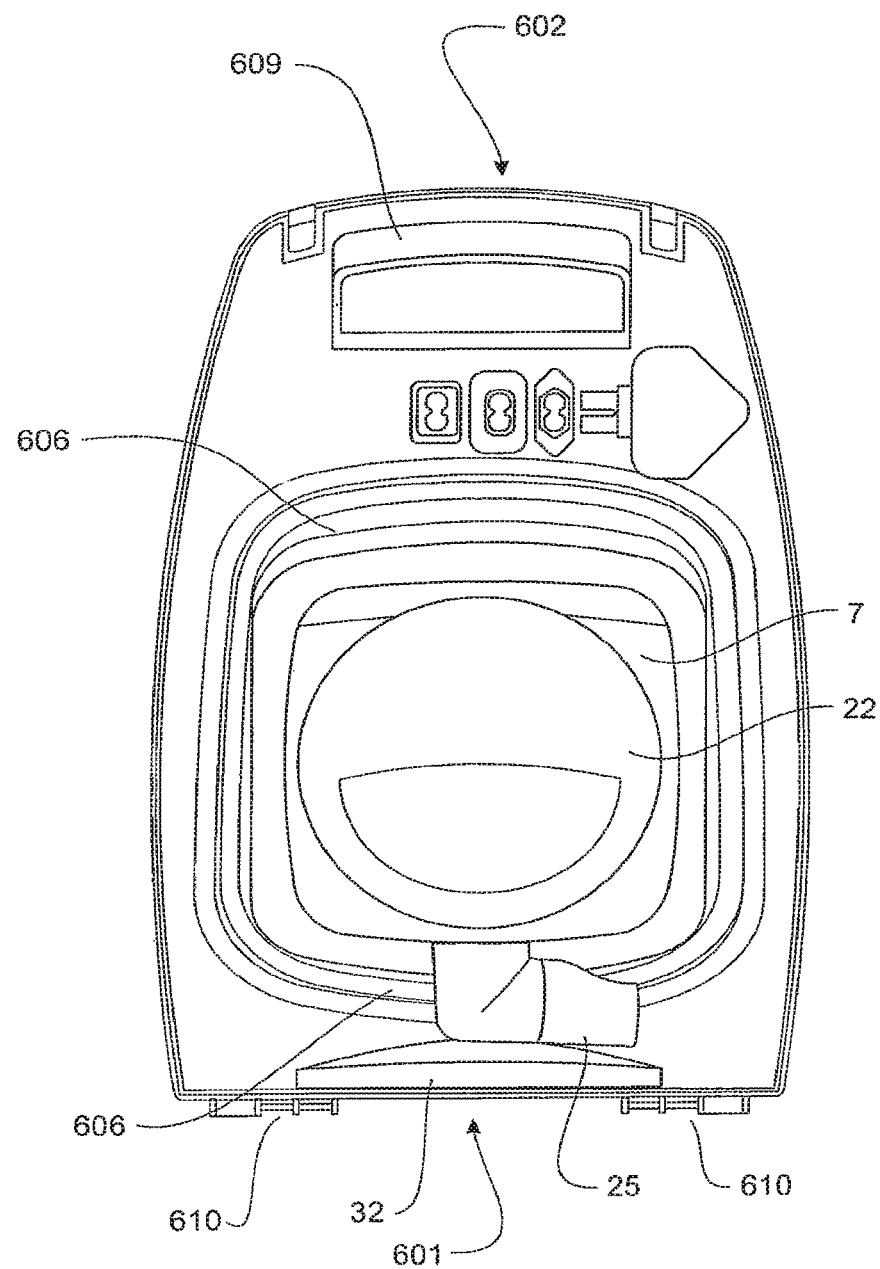
FIG. 20 shows a top view of the carry case of FIGS. 18 and 19, with the lid or top half not shown, and an integrated breathing assistance apparatus of the type shown in FIG. 3 located in the carry case ready for transport.

The carry case 600 is shown in FIGS. 18-20. The carry case 600 is formed from a rigid plastic in the preferred embodiment. The case 600 in the preferred form comes in two parts or halves, an upper half 604 and a lower half 605 ('half' is used in this context as a term of convenience and does not necessarily indicate that the upper and lower halves are required to be exactly or even close to the same size). In the closed position, the carry case 600 has one generally flat end 601, with the opposite end 602 coming to a rounded point when viewed side on. It is preferred that end 602 includes a handle 609 to aid a user in transporting the case 600. In the preferred form, the handle 609 is formed when the case is closed, the upper and lower halves 604, 605 including apertures which align to form one aperture when the case is closed, a user gripping the handle portion thus formed. The parts that form the handle are preferably rounded, and sized to facilitate their acting as a handle. The case 600 can be stood upright and rested on the flat end, or end base 601, in use. Alternatively, the carry case can be rested on the side base 603 which forms the lower side of the lower half 605. It should be noted that 'upper' and 'lower' are only directional indicators when the carry case 600 is resting on the side base 603. The two halves are connected by hinges - the upper half 604 attached to the lower half 605 so that the case can be opened by e.g. rotating or pivoting the upper half 605 relative to the stationary lower half 605, with the case 600 resting on side base 603, for packing or unpacking. In the fully closed position, the edges of the two come together to enclose a volume of space or an internal volume of the case. The hinges are adapted to allow the two halves a full range of movement—e.g. substantially 180 degrees of rotation relative to one another. This allows the upper half 604 to be rotated far enough that its outer surface can rest on the same surface as the lower half 605, for example a table or similar, and a user can freely access the inside of the case. In the preferred embodiment, the hinges 610 are located at the flat end 601, and form part of the flat base in use. The inside contains packaging or padding 606, in the preferred form including a pocket or recess 608 formed by moulding and shaping the padding 606, so that the pocket 608 conforms generally to the external shape and dimensions of the blower unit 7, so that at least the lower portion of the blower unit can be placed in the recess 608 in the packaging 606 in an upright position, with the packaging or padding 606 partially enclosing at least the lower portion of the blower unit 7, to hold the blower unit 7 securely in position during transport. As described above, the preferred form of chamber 31 is a top fill chamber with a removable lid 32. To prevent the user from inadvertently packing their integrated unit 6 away with chamber 31 still partially full and containing liquid, the carry case 600 is adapted in the following manner so that the case 600 cannot be closed fully if the lid 32 is still in position on the chamber 31. It should be noted that different forms of the carry case could be used to transport other types of systems that provide heated, humidified gases to a user. For example, systems that have push fit chambers filled through their inlets or outlets, rather than through a top fill aperture.

When the user needs to transport their integrated blower/humidifier unit, the user packs the integrated unit 6 in the carry case 600 by placing the integrated unit 6 in recess 608 in the packaging 606, the recess 608 shaped to enclose at least the base of the integrated unit 6. It is intended that the case 600 is as compact as possible. This helps a user to transport their unit as, for example, hand luggage on an aircraft, as it can be fitted in an overhead locker. Therefore, in the preferred form, the humidifier chamber 31 is located in the same position in which it is used in the blower 7, and not in a separate recess. The upper half 604 of the case 600 includes at least one protrusion 607 extending inwards from the inner surface of the upper half 604 (i.e. downwards towards lower half 605). The at least one protrusion 607 is sized and shaped so that the upper half and lower half 604, 605 cannot be brought fully together (i.e. the case 600 cannot be closed) when the humidifier chamber lid 32 is still in position on the chamber 31. When the humidifier chamber lid 31 is removed, the protrusion or protrusions 607 fit down inside the chamber 31. The lid 32 therefore has to be removed from the chamber 31 before the carry case 600 can be shut. It is preferred that the separate handle 22 can be located onto the blower unit 7, with the protrusion or protrusions 607 extending past the handle 22 to extend downwards into the chamber 31. The carry case 600 is preferably adapted to include an internal pocket or similar—e.g. in the packaging 606—which the user can use to store the lid 32 for travel.

It is preferred that the carry case can also be fitted with a strap or straps, to allow it to be carried in the same manner that a daysack or small knapsack would be carried, or slung over one shoulder and carried by one strap.

It should be noted that blower unit 7 is used as an example for the above described preferred form of carry case. In other, alternative forms, the carry case is adapted to carry respiratory humidification systems of the type where the humidifier chamber and the blower unit rigidly mate. In this alternative form, the padding includes a first pocket and a second pocket. The first pocket is adapted to enclose at least the base of the blower unit, and the second pocket is adapted to at least partly enclose the humidifier chamber. The two pockets are separate, so that the humidifier chamber must be disconnected from the blower before the chamber and the blower can be placed in their respective pockets. That is, the blower and the chamber cannot be mated to be correctly stored in the case in their respective pockets. The inner surface of the upper half includes a protrusion, facing inwards. When the case is closed, the protrusion locates into a space adjacent to the blower pocket, and ensures that the blower cannot be placed into the first pocket with the chamber rigidly mated to the blower, and the lid them closed. The protrusion will interfere with the chamber if a user attempts to close the lid while the chamber is in position on the blower.

LIST OF FEATURES

1. Prior art blower
2. Prior art chamber
3. User/Patient
4. User interface
5. Prior art integrated blower/humidifier
6. Integrated unit of the invention
7. Blower of the invention
8. Control knob
9. Display
10. Chamber seal
11. Humidifier compartment
12. Humidifier chamber
13. Blower inlet port
14. Blower outlet port
15. Humidifier chamber port (inlet)
16. Humidifier chamber port (outlet)
17.
18.
19. Electrical connector
20.
21. Prior art conduit from chamber to patient
22. Locking handle
23. Heater base
24. Rim of humidifier compartment
25. Patient outlet (connector)
26. Mating locking grooves
27. Mating lugs
28. Entry point of locking grooves
29.
30. Grip
31. Humidifier unit of the invention
32. Humidifier chamber lid
33. Ledge
34. Entry passage
35. Baffle
36. Exit Passage
37. Front faceplate
38. Depression
39. Mechanical fastener—clips
40.
41. Prior art conduit between blower and chamber
42.
44. Connector Board
45. Ring magnet
46. Magnetised sections
47.
48. Magnet
49. Magnet
50. Front face of (7)
51. Axis of rotation
52.
53.
54.
55.
56.
60. Fastener tips
61. Button
62. Boss
63. Fasteners
70. Silicone seal
80. Rear wall
100. Fan unit
101. Air inlet vent
102.
103.
104.
105.
106.
107.
108.
109.
110. Fan entry aperture
111. Magnetic segments
112. Coils
113. Bearing unit
120. Duct
121. Blower exit
130. Air path
200. Air entry passage
201. Exit aperture
202. Umbrella portion
300. Control circuitry
400. Recess
500. Power supply sub-housing
501. Power supply board
502. Sub housing side wall (outer)
503. Sub housing top wall
504. Sub housing side wall (inner)
505. Curved path
506. Aperture
510. Sub housing range face
600. carry case
601. carry case flat end
602. carry case pointed end
604. carry case upper half
605. carry case lower half
606. carry case packaging
607. carry case lid protrusion
608. carry case recess
609. carry case handle
610. carry case hinges
1000. Aperture

What is claimed is:

1. A humidifier system comprising:
   an outlet for providing heated humidified gases to a user,
   a connector coupled to the outlet, the connector adapted to allow simultaneous combined pneumatic and electrical connections between an assisted breathing unit and an outlet conduit, wherein the electrical and pneumatic connections are made at the outlet, the connector comprising a conduit for a flow of heated humidified gases, the connector comprising an electrical connector, wherein at least a portion of the electrical connector is spaced apart and separate from the conduit for the flow of heated humidified gases, the electrical connector configured to electrically connect the assisted breathing unit and the outlet conduit, and wherein the connector comprises an elbow rotatable about the outlet to change an orientation of the outlet conduit relative to the assisted breathing unit.

2. The humidifier system of claim 1, wherein the connector comprises an electrical connector parallel to a pneumatic connector.

3. The humidifier system of claim 1, further comprising an outer housing.

4. The humidifier system of claim 3, wherein the connector is coupled to the outer housing.

5. The humidifier system of claim 1, further comprising the assisted breathing unit.

6. The humidifier system of claim 5, wherein the assisted breathing unit comprises a humidifier chamber.

7. The humidifier system of claim 6, wherein the outlet is an outlet of the humidifier chamber, and the connector is coupled to the outlet of the humidifier chamber.

8. The humidifier system of claim 1, wherein the connector faces upwards in use for ease of connection with the outlet conduit.

9. The humidifier system of claim 1, further comprising the outlet conduit.

10. An integrated blower and humidification system comprising:
    an outlet for providing heated humidified gases to a user,
    a connector coupled to the outlet, the connector adapted to allow simultaneous combined pneumatic and electrical connections between an assisted breathing unit and an outlet conduit, wherein the electrical and pneumatic connections are made at the outlet, the connector comprising a tubular portion for a flow of heated humidified gases, the connector comprising an electrical connector, wherein at least a portion of the electrical connector is spaced apart and separate from the tubular portion for the flow of heated humidified gases, the electrical connector configured to electrically connect the assisted breathing unit and the outlet conduit, and wherein the connector comprises an elbow rotatable about the outlet to change an orientation of the outlet conduit relative to the assisted breathing unit.

11. The integrated blower and humidification system of claim 10, wherein the connector comprises an electrical connector parallel to a pneumatic connector.

12. The integrated blower and humidification system of claim 10, further comprising an outer housing, wherein the connector is coupled to the outer housing.

13. The integrated blower and humidification system of claim 10, further comprising the assisted breathing unit.

14. The integrated blower and humidification system of claim 13, wherein the assisted breathing unit comprises a humidifier chamber.

15. The integrated blower and humidification system of claim 14, wherein the outlet is an outlet of the humidifier chamber, and the connector is coupled to the outlet of the humidifier chamber.

16. The integrated blower and humidification system of claim 10, wherein the connector faces upwards in use for ease of connection with the outlet conduit.

17. The integrated blower and humidification system of claim 10, further comprising the outlet conduit.

18. A connector for connecting an integrated humidification system to an outlet conduit for providing heated humidified gases to a user, the connector comprising:
    a pneumatic connector adapted to allow a pneumatic connection between the integrated humidification system and the outlet conduit,
    an electrical connector adapted to allow an electrical connection between the integrated humidification system and the outlet conduit, and
    wherein the connector is configured to be coupled to an outlet of the integrated humidification system, wherein the electrical and pneumatic connections are made at the outlet, the connector comprising a conduit for a flow of heated humidified gases, wherein at least a portion of the electrical connector is spaced apart and separate from the conduit for the flow of heated humidified gases, the electrical connector configured to electrically connect an assisted breathing unit and the outlet conduit, wherein the connector comprises an elbow rotatable about the outlet to change an orientation of the outlet conduit relative to the assisted breathing unit,
    wherein the connector is adapted to allow simultaneous combined pneumatic and electrical connections.

19. The connector of claim 18, wherein the electrical connector is parallel to the pneumatic connector.

20. The connector of claim 18, further comprising the outlet conduit.

* * * * *